(12) United States Patent
Xiao et al.

(10) Patent No.: US 11,773,384 B2
(45) Date of Patent: Oct. 3, 2023

(54) CHIMERIC ANTIGEN RECEPTOR (CAR) AND T CELL RECEPTOR (TCR) MODIFIED T CELLS

(71) Applicant: Innovative Cellular Therapeutics Holdings, Ltd., Grand Cayman (KY)

(72) Inventors: Lei Xiao, Rockville, MD (US); Li Mao, Shanghai (CN); Zhao Wu, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 219 days.

(21) Appl. No.: 17/233,935

(22) Filed: Apr. 19, 2021

(65) Prior Publication Data

US 2021/0238568 A1    Aug. 5, 2021

Related U.S. Application Data

(63) Continuation of application No. 16/157,545, filed on Oct. 11, 2018, now Pat. No. 11,008,556.

(60) Provisional application No. 62/571,413, filed on Oct. 12, 2017.

(51) Int. Cl.
| | | |
|---|---|---|
| *C12N 9/22* | (2006.01) |
| *A61K 35/17* | (2015.01) |
| *A61P 35/00* | (2006.01) |
| *C12N 9/10* | (2006.01) |
| *C12N 15/62* | (2006.01) |
| *C12N 15/52* | (2006.01) |

(52) U.S. Cl.
CPC ............. *C12N 9/22* (2013.01); *A61K 35/17* (2013.01); *A61P 35/00* (2018.01); *C12N 9/10* (2013.01); *C12N 15/52* (2013.01); *C12N 15/625* (2013.01); *C12Y 301/21* (2013.01); *C07K 2319/81* (2013.01)

(58) Field of Classification Search
CPC .......... C12N 9/10; C12N 15/52; A61K 35/17
See application file for complete search history.

(56) References Cited

U.S. PATENT DOCUMENTS

| | | | | |
|---|---|---|---|---|
| 11,008,556 B2* | 5/2021 | Xiao | .............. | C12Y 301/21 |
| 2019/0125798 A1 | 5/2019 | Xiao et al. | | |
| 2020/0158716 A1 | 5/2020 | Shalek et al. | | |

* cited by examiner

*Primary Examiner* — Tekchand Saidha
(74) *Attorney, Agent, or Firm* — Lee & Hayes, P.C.

(57) ABSTRACT

The present disclosure relates to compositions and methods for compositions, methods, and kits for treating cancer using modified T cells in which TRAC genes are inactivated using a Zinc-finger nuclease (ZFN). The ZFN may include a first zinc finger protein (ZFP) that binds a first target site in a T-cell receptor alpha constant (TRAC) gene and a second ZFP that binds a second target site in the TRAC gene.

22 Claims, 8 Drawing Sheets

Specification includes a Sequence Listing.

CHIMERIC ANTIGEN RECEPTOR (CAR) AND T CELL RECEPTOR (TCR) MODIFIED T CELLS

CROSS REFERENCE TO RELATED PATENT APPLICATIONS

This application is a continuation of co-pending U.S. patent application Ser. No. 16/157,545, filed Oct. 11, 2018, which claims the benefit of U.S. Provisional Patent Application No. 62/571,413, filed on Oct. 12, 2017, all of which are hereby incorporated by reference in their entirety

SEQUENCE LISTING INFORMATION

A computer readable textfile, entitled Sequence-Listing-ST25.txt," created on or about Apr. 6, 2021, with a file size of about 50.4 KB, contains the sequence listing for this application and is hereby incorporated by reference in its entirety.

TECHNICAL FIELD

The present disclosure relates to modified cells and uses, in particular to compositions and methods for preparing modified cells and treating cancer using the modified cells.

BACKGROUND

Chimeric antigen receptors (CARs) for expression on T cells were developed more than 25 years ago. CARs are an application that combines an antigen recognition domain of a specific antibody with an intracellular domain of TCR. T cells genetically targeted to certain malignancies have demonstrated tremendous clinical outcomes. During CAR T cell therapy, a physician draws blood to harvest the patient's cytotoxic T cells. The cells are re-engineered in a lab to attack the patient's particular cancer cells. However, this autologous T cell immunotherapy has its limitations, especially when some patients are not able to generate enough T cells for continuous CART cell therapy.

SUMMARY

Embodiments of the present disclosure relate to an isolated zinc finger nuclease (ZFN) comprising a first zinc finger protein (ZFP) that binds a first target site in a T cell receptor alpha constant (TRAC) gene, a second ZFP that binds a second target site in the TRAC gene, and a cleavage domain. The first ZFP may include three or more zinc finger domains, and the second ZFP may include three or more zinc finger domains. Some embodiments relate to an isolated cell comprising an isolated nucleic acid sequence encoding a CAR, wherein the TRAC gene is inactivated using the ZFN described above. Some embodiments relate to a method of treating cancer in a subject. The method may include administering a genetically modified cell to the subject, and the cancer is selected from the group consisting of a lung carcinoma, pancreatic cancer, liver cancer, bone cancer, breast cancer, colorectal cancer, leukemia, ovarian cancer, lymphoma, and brain cancer.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
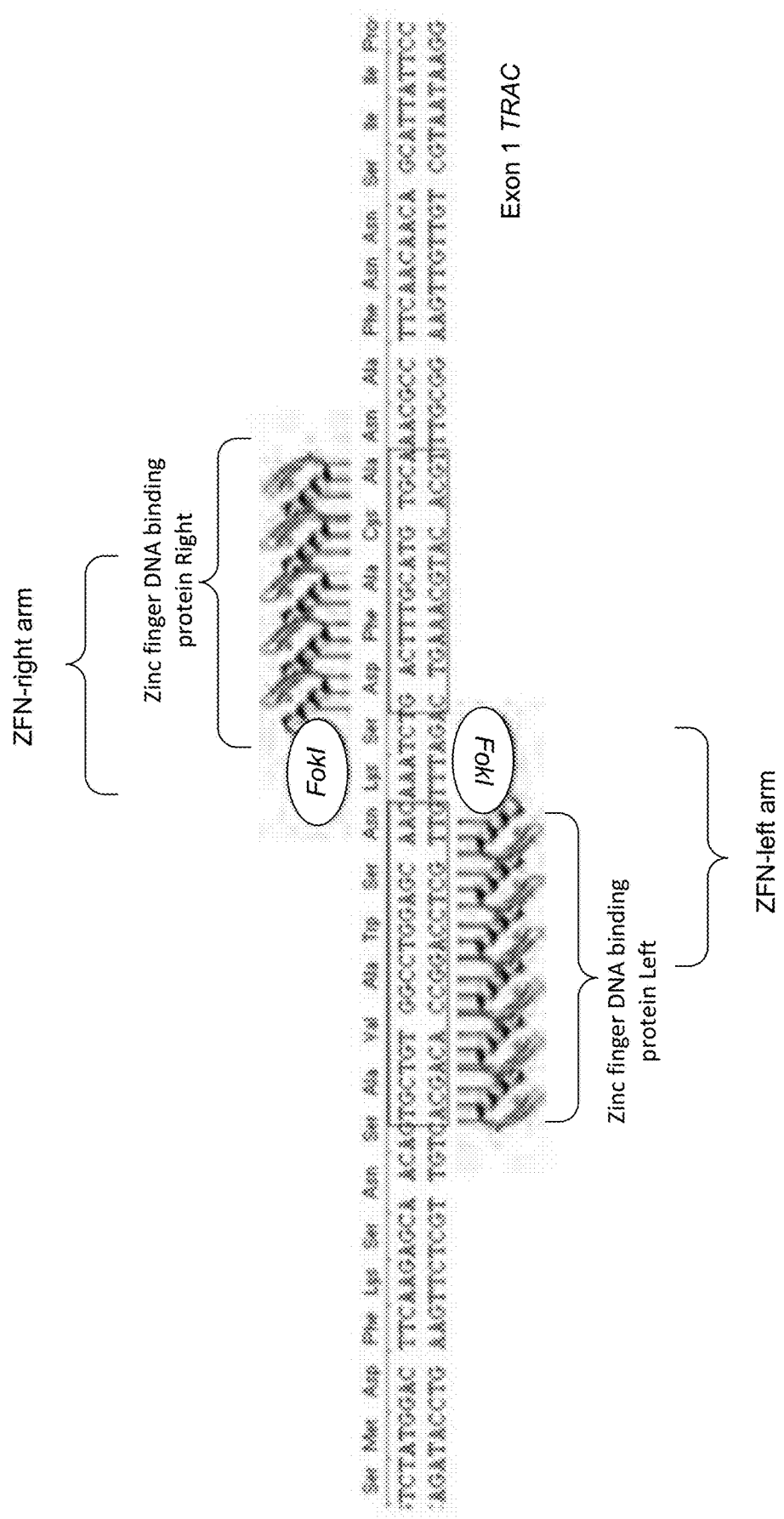
FIG. 1 illustrates an example of a pair of ZFNs targeting Exon 1 of TRAC (amino acid sequence SEQ ID NO.: 45 and nucleic acid sequence SEQ ID NO.: 46).
Figure 2:
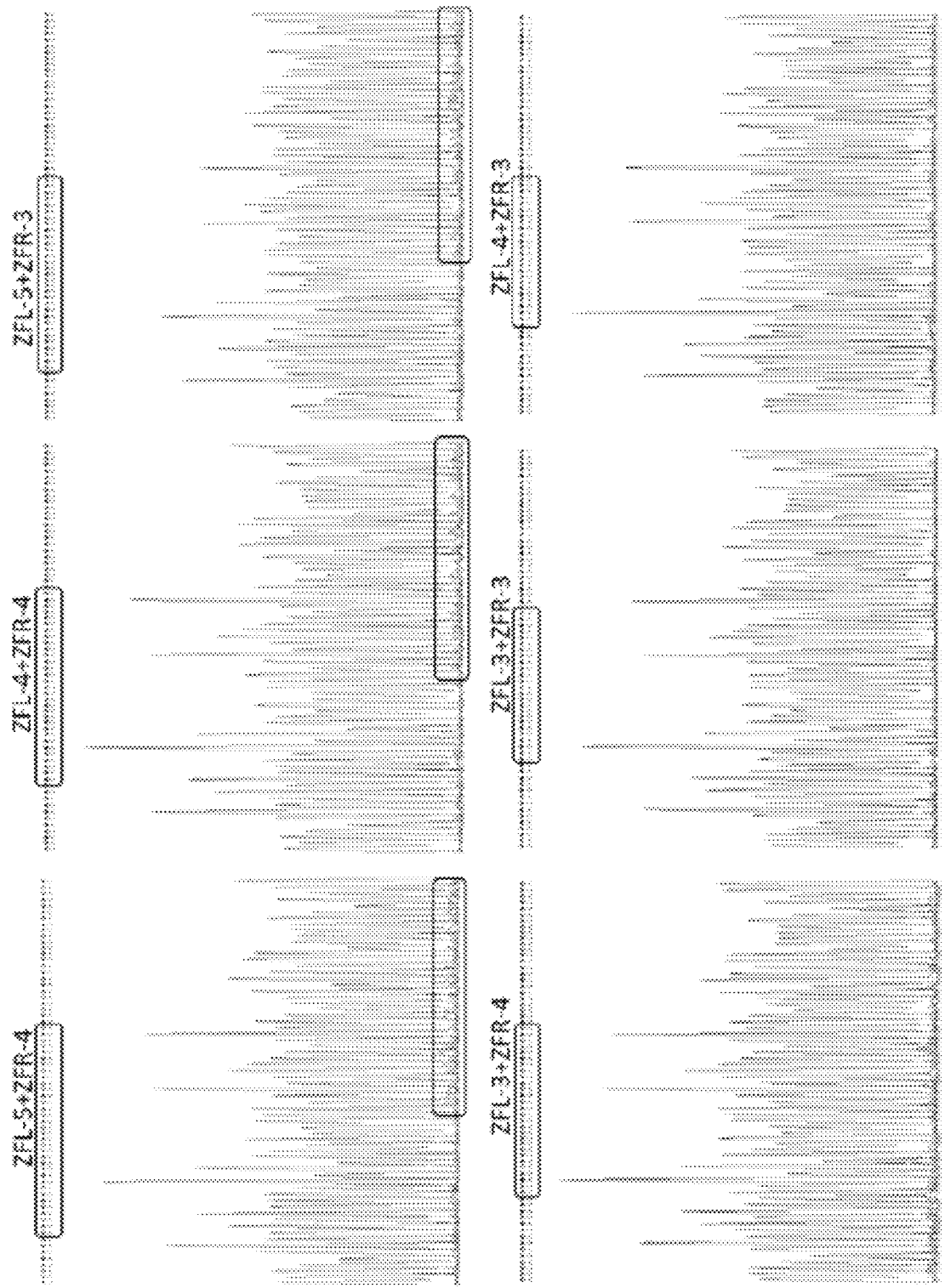
FIGS. 2, 3, 4, 5, 6, 7, and 8 show sequencing results for ZFNs that target TRAC gene fragments and are amplified by PCR. Double sequencing signals are observed for the ZFNs, and the bottom portions of double sequencing signals are shown with black boxes, suggesting that the targeting gene was introduced with a mutation. The higher the density of the double sequencing signals, indicates the higher the editing efficiency. Labels above the sequencing results represent corresponding ZFN combinations, and target sequences identified by ZFNs are shown with black boxes.
Figure 3:
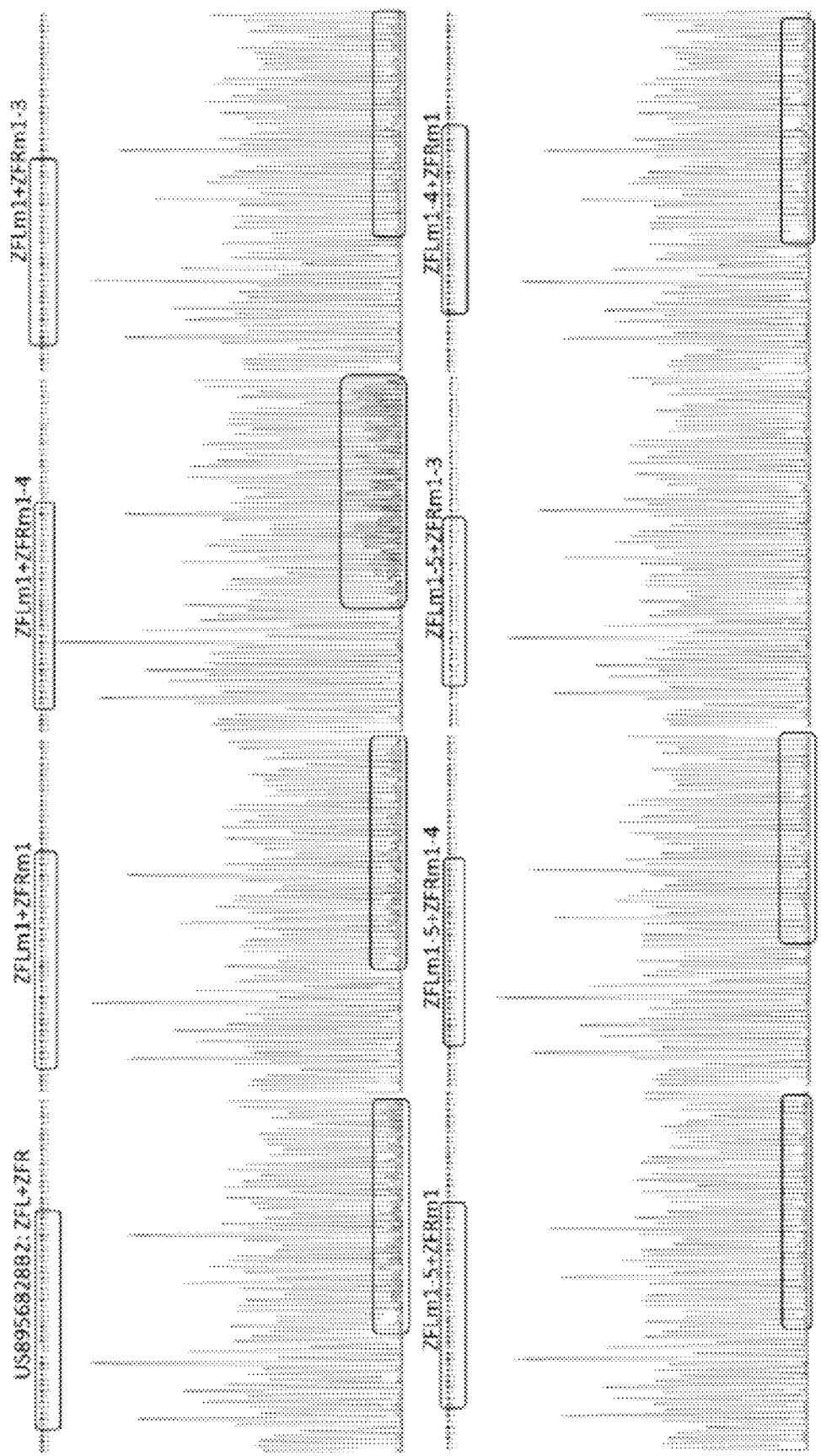
Figure 4:
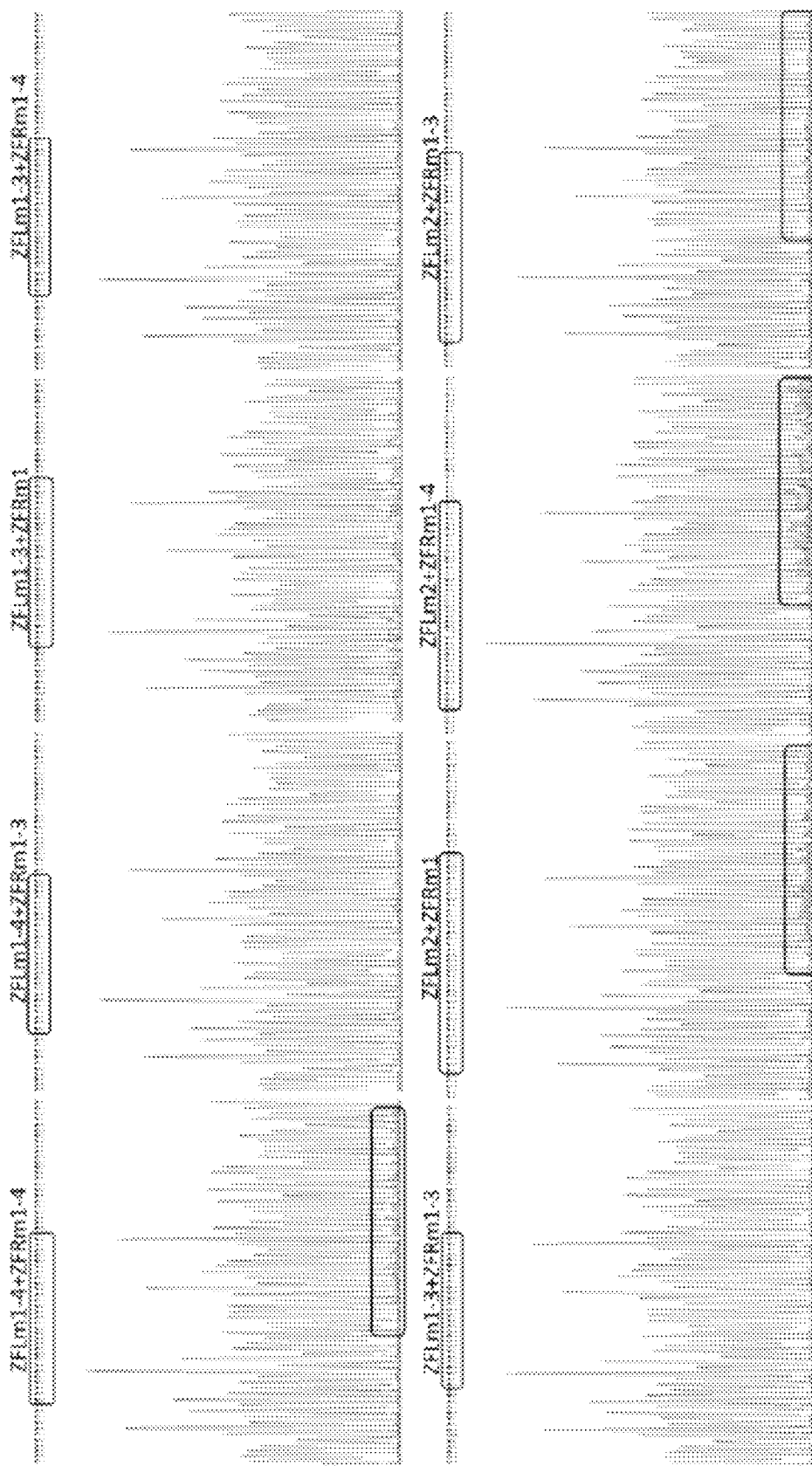
Figure 5:
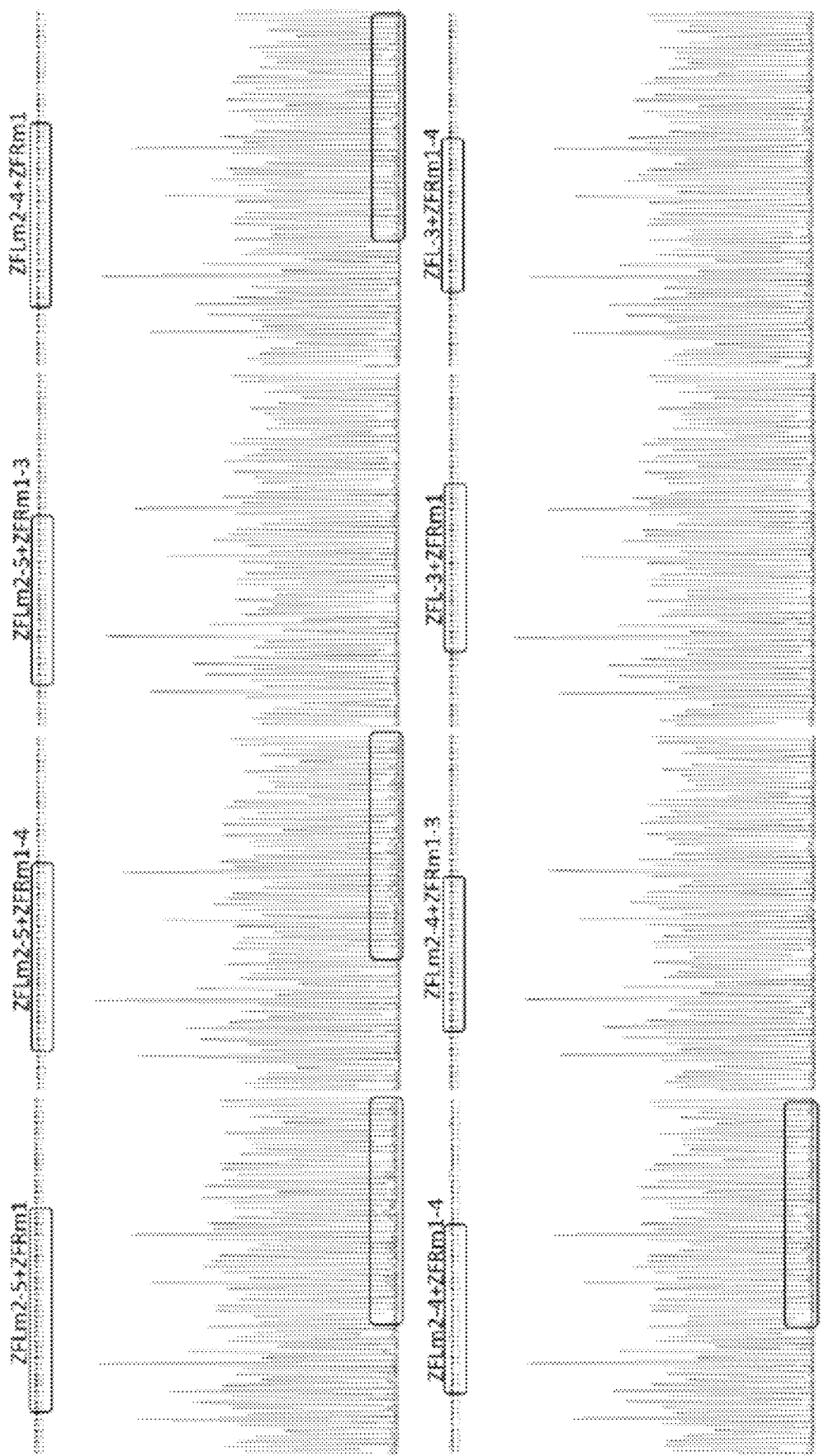
Figure 6:
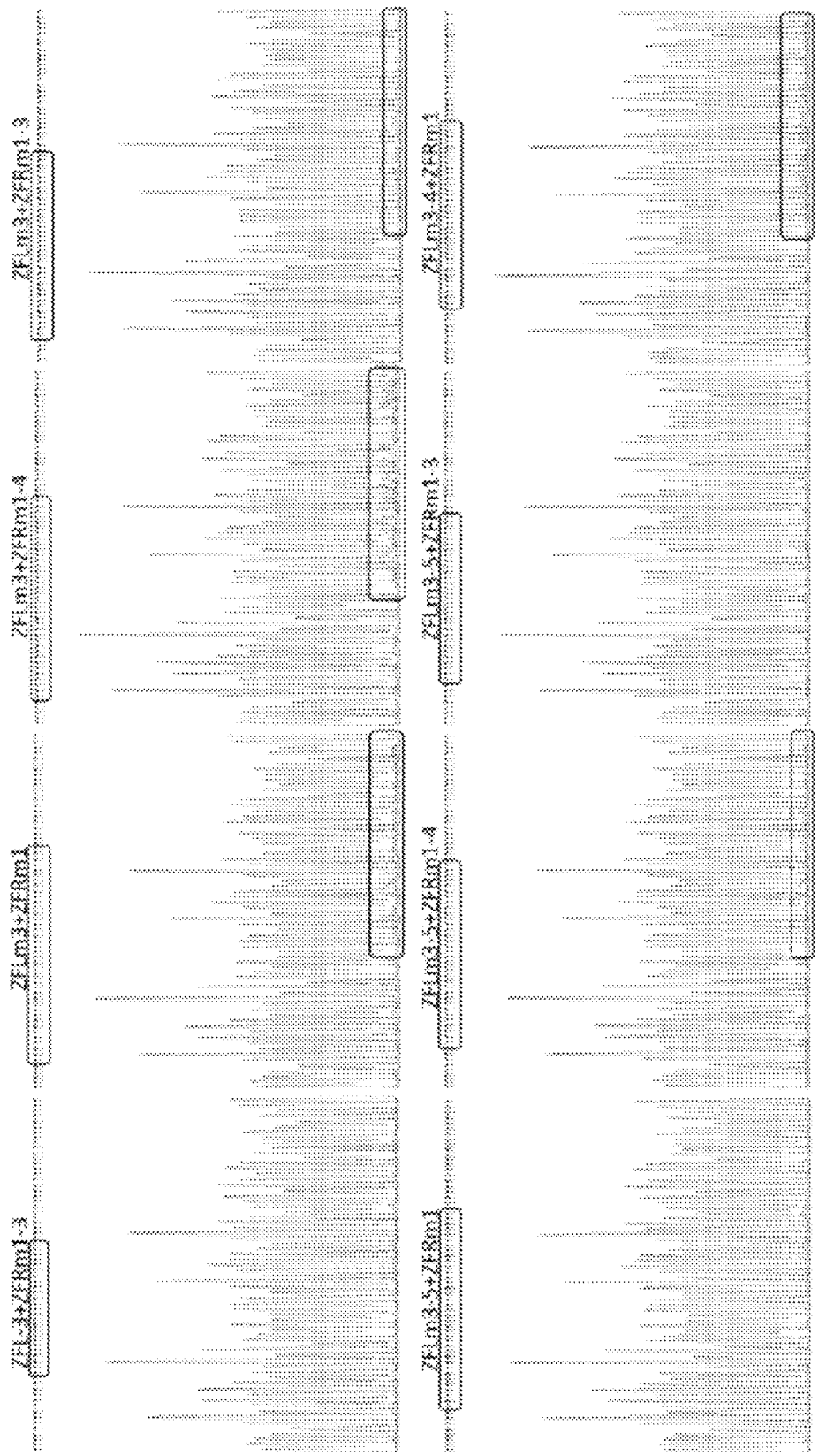
Figure 7:
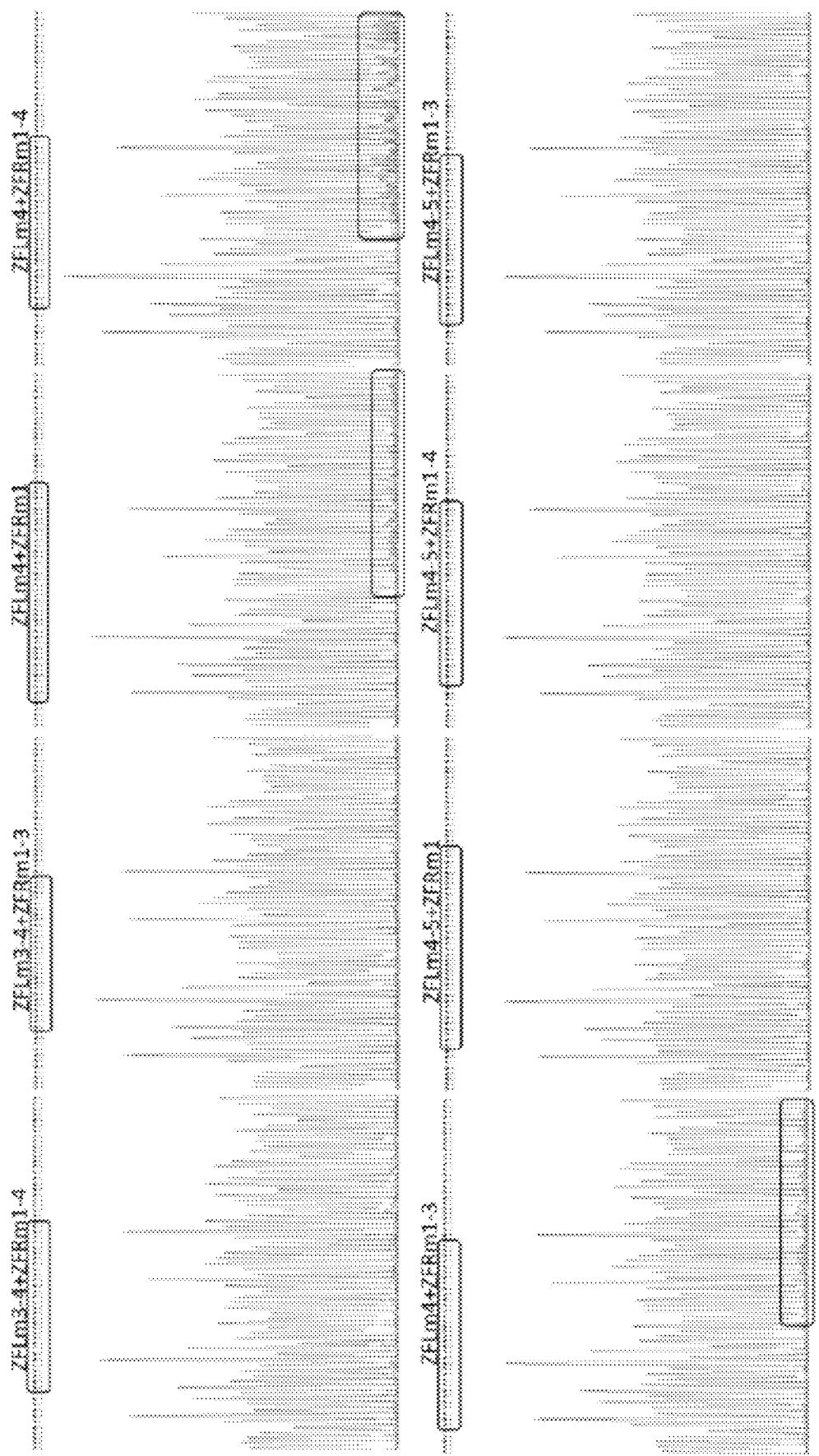
Figure 8:
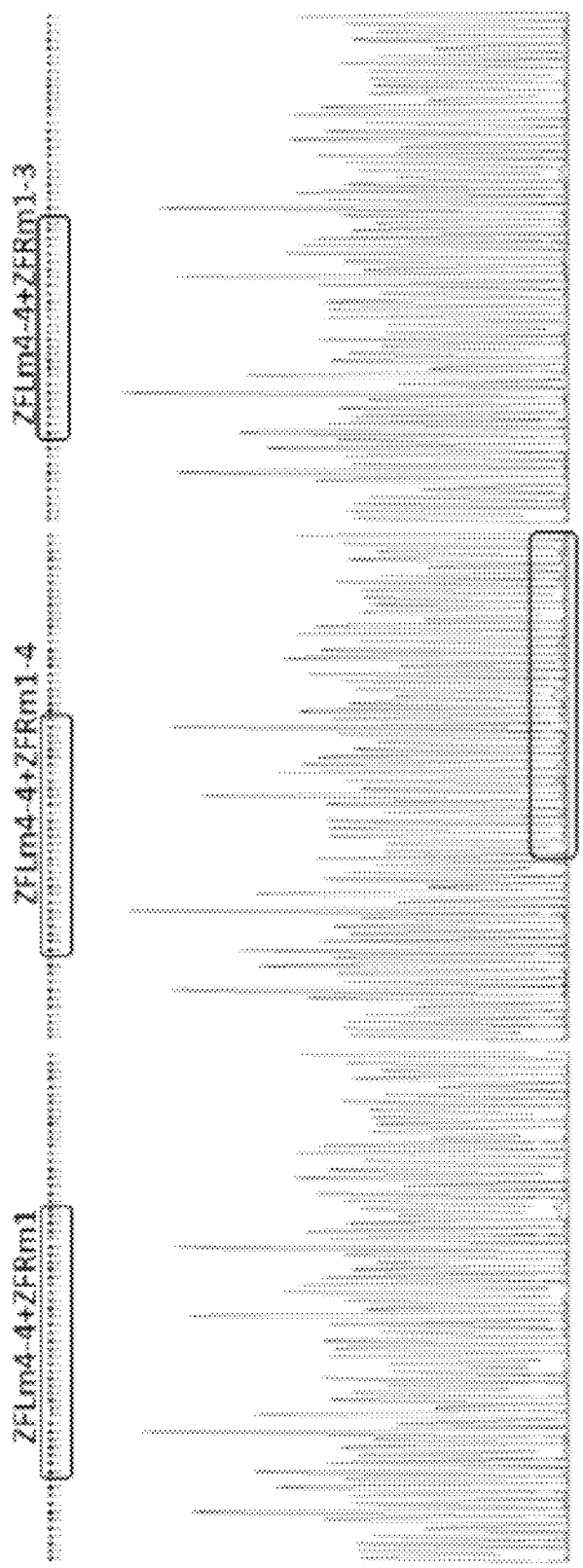

The present disclosure relates, in part, to the demonstration that endogenous TRAC of CAR T cells may be modified using specific ZFNs, and designs of these specific ZFNs determine the probability and/or efficiency of the modifications.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and X light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be a related or unrelated or recipient subject, but the donor subject has immune system markers which are similar to the recipient subject.

The term "xenogeneic" is used to describe a graft derived from an subject of a different species. As an example, the donor subject is from a different species than a recipient subject and the donor subject and the recipient subject can be genetically and immunologically incompatible.

The term "cancer" as used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any elements listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared x100. For example, if 6 of 10 of the positions in two sequences are matched or homologous then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially frr from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In some embodiments, the cells are cultured in vitro. In other embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumor or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any human, animal, or living organism, amenable to the methods described herein. In certain non-limiting embodiments, the patient, subject, or individual is a human or animal. In some embodiments, the term "subject" is intended to include living organisms in which an immune response can be elicited (e.g., mammals). Examples of subjects include humans, and animals such as dogs, cats, mice, rats, and transgenic species thereof.

A subject in need of a treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes), as illustrated in FIG. 1.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease. Exemplary target sites for various targeted ZFPs are shown in Table 1.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-$\beta$, and/or reorganization of cytoskeletal structures. CD3 zeta is not the only suitable primary signaling domain for a CAR construct with respect to the primary response. For example, back in 1993, both CD3 zeta and FcR gamma were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T-cell receptors" PNAS, 1993 Jan. 15; 90(2):720-4, showed that two CAR constructs in which an scFv was fused to "either the FcR y chain or the CD3 complex s chain" triggered T cell activation and target cell. Notably, as demonstrated in Eshhar et al., CAR constructs containing only the primary signaling domain CD3 zeta or FcR gamma are functional without the co-presence of costimulatory domains. Additional non-CD3 zeta based CAR constructs have been developed over the years. For example, Wang et al., "A Chimeric Antigen Receptor (CARS) Based Upon a Killer Immunoglobulin-Like Receptor (KIR) Triggers Robust Cytotoxic Activity in Solid Tumors" Molecular Therapy, vol. 22, no. Suppl.1, May 2014, page S57, tested a CAR molecule in which an scFv was fused to "the transmembrane and cytoplasmic domain of a killer immunoglobulin-like receptor (KIR). Wang et al. states that, "a KIR-based CAR targeting mesothelin (SS 1-KIR) triggers antigen-specific cytotoxic activity and cytokine production that is comparable to CD3$^-$-based CARS." A second publication from the same group, Wang et al., "Generation of Potent T-cell Immunotherapy for Cancer Using DAP12-Based, Multichain, Chimeric Immunoreceptors" Cancer Immunol Res. 2015 July; 3(7):815-26, showed that a CAR molecule in which "a single-chain variable fragment for antigen recognition [was fused] to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Embodiments of the present disclosure relate to an isolated zinc finger nuclease (ZFN) comprising a first zinc finger protein (ZFP) that binds a first target site in a T-cell receptor alpha constant (TRAC) gene, a second ZFP that binds a second target site in the TRAC gene, and a cleavage domain. The first ZFP may include three or more zinc finger domains, and the second ZFP may include three or more zinc finger domains.

Some embodiments of the present disclosure relate to a Zinc Finger Nuclease (ZFN) comprising zinc finger DNA binding proteins and a DNA-cleaving domain comprising a cleavage domain and/or a cleavage half-domain.

The zinc finger DNA binding proteins (or ZFP) may include 1, 2, 3, 4, 5, 6 or more zinc fingers, each zinc finger having a recognition helix that binds a target subsite in the target gene. In certain embodiments, the zinc finger DNA binding proteins (or ZFPs) comprise 3, or 4 or 5 or 6 zinc fingers (wherein each zinc finger comprises one or more DNA binding domains (or zinc finger domains) designated as F1, F2, F3, F4, F5 and F6 and ordered F1 to, F2, F3, F4, F5, or F6 from N-terminus to C-terminus) and the fingers comprise the amino acid sequence of the recognition helix shown in Table 1.

The cleavage domain and/or a cleavage half-domain for example, can include a wild-type or engineered FokI cleavage half-domain. In some embodiments, the nuclease domain may comprise a wild-type nuclease domain or nuclease half-domain (e.g., a FokI cleavage half-domain). In some embodiments, the cleavage domain and/or a cleavage half-domain comprises engineered (non-naturally occurring) nuclease domains or half-domains, for example, engineered FokI cleavage half-domains that form obligate heterodimers.

In some embodiments, the first ZFP comprises amino acid sequences in the following order: SEQ ID NOS.: 2, 5-7, 2, and 19, from the N-terminus to the C-terminus of the first ZFP, and the second ZFP comprising amino acid sequences in the following order: SEQ ID NOS.: 2, 1-3 and 22, from the N-terminus to the C-terminus of the second ZFP; the first ZFP comprises amino acid sequences in the following order: SEQ ID NOS.: 2, 5-7, 2, and 19, from the N-terminus to the C-terminus of the first ZFP, and the second ZFP comprises amino acid sequences in the following order: SEQ ID NOS.: 1-3, and 22, from the N-terminus to the C-terminus of the second ZFP; the first ZFP comprises amino acid sequences in the following order: SEQ ID NOS.: 2, 5, 11, 7, 2, and 9, from the N-terminus to the C-terminus of the first ZFP, and the second ZFP comprises amino acid sequences in the following order: SEQ ID NOS.: 2, 1-3, and 22, from the N-terminus to the C-terminus of the first ZFP, and the second ZFP comprises amino acid sequences SEQ ID NOS.: 1-3, and 22, from the N-terminus to the C-terminus of the second ZFP; the first ZFP comprises amino acid sequences in the following order SEQ ID NOS.: 2, 5, 15, 7, 2, and 9, from the N-terminus to the C-terminus of the first ZFP, and the second ZFP comprises amino acid sequences in the following order: SEQ ID NOS.: 2, 1-3 and 22, from the N-terminus to the C-terminus of the second ZFP; the first ZFP comprises amino acid sequences SEQ ID NOS.: 2, 5, 15, 7, 2, and 9, from the N-terminus to the C-terminus of the first ZFP, and the second ZFP comprises amino acid sequences in the following order: SEQ ID NOS.: 1-3, and 22, from the N-terminus to the C-terminus of the second ZFP; or the first ZFP comprises amino acid sequences in the following order: SEQ ID NOS.: 2, 5, 23, and 7, 2, and 9, from the N-terminus to the C-terminus of the first ZFP, and the second ZFP comprises amino acid sequences in the following order: SEQ ID NOS.: 1-3, and 22, from the N-terminus to the C-terminus of the second ZFP.

In these instances, the percentage of cells introduced with ZFN described herein and having ZFN mediated gene modification, such as genome editing, is more than 20.

In some embodiments, the first ZFP is ZFL-5, and the second ZFP is ZFR-4; the first ZFP is ZFL-5, and the second ZFP is ZFR-3; the first ZFP is ZFL-4, and the second ZFP is ZFR-4; the first ZFP is ZFLm1, and the second ZFP is ZFRm1; the first ZFP is ZFLm1, and the second ZFP is ZFRm1-4; the first ZFP is ZFLm1, and the second ZFP is ZFRm1-3; the first ZFP is ZFLm1-5, and the second ZFP is ZFRm1; the first ZFP is ZFLm1-5, and the second ZFP is ZFRm1-4; the first ZFP is ZFLm1-4, and the second ZFP is ZFRm1; the first ZFP is ZFLm1-4, and the second ZFP is ZFRm1-4; the first ZFP is ZFLm2, and the second ZFP is ZFRm1; the first ZFP is ZFLm2, and the second ZFP is ZFRm1-4; the first ZFP is ZFLm2, and the second ZFP is ZFRm1-3; the first ZFP is ZFLm2-5, and the second ZFP is ZFRm1; the first ZFP is ZFLm2-5, and the second ZFP is ZFRm1-4; the first ZFP is ZFLm2-4, and the second ZFP is ZFRm1; the first ZFP is ZFLm2-4, and the second ZFP is ZFRm1-4; the first ZFP is ZFLm3, and the second ZFP is ZFRm1; the first ZFP is ZFLm3, and the second ZFP is ZFRm1-4; the first ZFP is ZFLm3, and the second ZFP is ZFRm1-3; the first ZFP is ZFLm3-5, and the second ZFP is ZFRm1-4; the first ZFP is ZFLm3-4, and the second ZFP is ZFRm1; the first ZFP is ZFLm4, and the second ZFP is ZFRm1; the first ZFP is ZFLm4, and the second ZFP is ZFRm1-4; the first ZFP is ZFLm4, and the second ZFP is ZFRm1-3; or the first ZFP is ZFLm4-4, and the second ZFP is ZFRm1-4. All of these zinc finger binding proteins are further described in Table 1.

Some embodiments relate to an isolated ZFN comprising a first ZFP that binds a first target site in a TRAC gene, a second ZFP that binds a second target site in the TRAC gene, and a cleavage domain. In some embodiments, the first target site comprises a nucleic acid sequence SEQ ID NO.: 13, and the second target site comprises anucleic acid sequence SEQ ID NO.: 10; the first target site comprises a nucleic acid sequence SEQ ID NO.: 13, and the second target site comprises a nucleic acid sequence SEQ ID NO.: 43 (GACTTTGCA); the first target site comprises a nucleic acid sequence SEQ ID NO.: 14, and the second target site comprises a nucleic acid sequence SEQ ID NO.: 10; the first target site comprises a nucleic acid sequence SEQ ID NO.: 20, and the second target site comprises a nucleic acid sequence SEQ ID NO.: 10; the first target site comprises a nucleic acid sequence SEQ ID NO.: 20, and the second target site comprises a nucleic acid sequence SEQ ID NO.: 43 (GACTTTGCA); the first target site comprises a nucleic acid sequence SEQ ID NO.: 13, and the second target site comprises a nucleic acid sequence SEQ ID NO.: 21; the first target site comprises a nucleic acid sequence SEQ ID NO.: 13, and the second target site comprises a nucleic acid sequence SEQ ID NO.: 10; the first target site comprises a nucleic acid sequence SEQ ID NO.: 14, and the second target site comprises a nucleic acid sequence SEQ ID NO.: 21; the first target site comprises a nucleic acid sequence SEQ ID NO.: 14, and the second target site comprises a nucleic acid sequence SEQ ID NO.: 10; the first target site comprises a nucleic acid sequence SEQ ID NO.: 20, and the second target site comprises an nucleic acid sequence SEQ ID NO.: 10; the first target site comprises a nucleic acid sequence SEQ ID NO.: 20, and the second target site comprises a nucleic acid sequence SEQ ID NO.: 43 (GACTTTGCA); the first target site comprises a nucleic acid sequence SEQ ID NO.: 13, and the second target site comprises a nucleic acid sequence SEQ ID NO.: 21; the first target site comprises a nucleic acid sequence SEQ ID NO.: 13, and the second target site comprises a nucleic acid sequence SEQ ID NO.: 10; the first target site comprises a nucleic acid sequence SEQ ID NO.: 14, and the second target site comprises a nucleic acid sequence SEQ ID NO.: 21; the first target site comprises a nucleic acid sequence SEQ ID NO.: 14, and the second target site comprises a nucleic acid sequence SEQ ID NO.: 10; the first target site comprises a nucleic acid sequence SEQ ID NO.: 20, and the second target site comprises a nucleic acid sequence SEQ ID NO.: 10; the first target site comprises a nucleic acid sequence SEQ ID NO.: 20, and the second target site comprises a nucleic acid sequence SEQ ID NO.: 43 (GACTTTGCA); the first target site comprises a nucleic acid sequence SEQ ID NO.: 13, and the second target site comprises a nucleic acid sequence SEQ ID NO.: 10; the first target site comprises a nucleic acid sequence SEQ ID NO.: 14, and the second target site comprises a nucleic acid sequence SEQ ID NO.: 21; the first target site comprises a nucleic acid sequence SEQ ID NO.: 20, and the second target site comprises a nucleic acid sequence SEQ ID NO.: 43 (GACTTTGCA); or the first target site comprises a nucleic acid sequence SEQ ID NO.: 14, and the second target site comprises a nucleic acid sequence SEQ ID NO.: 10.

In some embodiments, the TRAC gene that the ZFP binds to is a human TRAC gene. In some embodiments, the cleavage domain of the ZFN comprises a wild-type or engineered FokI cleavage domain. Some embodiments relate to a polynucleotide encoding the isolated ZFN described above. Some embodiments relate to a vector comprising the polynucleotide. In some embodiments, the vector is an adenoviral or lentiviral vector. Some embodiments relate to an isolated cell or a cell line comprising the isolated ZFN described above. In some embodiments, the isolated cell is a stem cell, a T cell or a Natural Killer (NK) cell. For example, the cell is a T cell derived from a primary human T cell isolated from a human donor. Some embodiments relate to isolated T cell that has a reduced expression of endogenous TRAC gene. In some embodiments, the isolated T cell lacks expression of a functional endogenous TCR and/or produces substantially impaired endogenous TCR on its surface such that the endogenous TCR will not substantially elicit an adverse immune reaction in a host, e.g., a GVHD reaction. In some instances, progeny of the T cell may also be reasonably expected to lack expression of a functional endogenous TCR and/or produces substantially impaired endogenous TCR on their surface such that the progeny of the endogenous TCR will not substantially elicit an adverse immune reaction in a host, e.g., a GVHD reaction. Whether a cell expresses a functional endogenous TCR may be determined using known assay methods such as are known in the art.

Some embodiments relate to a CAR T cell comprising an isolated nucleic acid sequence encoding a chimeric antigen receptor (CAR), and the endogenous TRAC gene has been inactivated in the CAR T cell using the ZFN described above to avoid GVHD and rejection. For example, the CART cell has a reduced expression of endogenous TRAC gene. In some embodiments, the CAR T cell lacks expression of a functional endogenous TCR and/or produces substantially impaired endogenous TCR on its surface such that the endogenous TCR will not substantially elicit an adverse immune reaction in a host, e.g., a GVHD reaction. In some instances, progeny of the CAR T cell may also be reasonably expected to lack expression of a functional endogenous TCR and/or produces substantially impaired endogenous TCR on their surface such that the progeny of the endogenous TCR will not substantially elicit an adverse immune reaction in a host, e.g., a GVHD reaction.

In some embodiments, the TCR is or is derived from a healthy human donor having HLA type that matches the recipient. Typically, matching is performed on the basis of variability at three or more loci of the HLA gene, and a perfect match at these loci is preferred. In some instances, allogeneic transplant donors may be related (usually a closely HLA matched sibling), syngeneic (a monozygotic 'identical' twin of the patient) or unrelated (donor who is not related and found to have very close degree of HLA matching). The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease. In other embodiments, endogenous HLA I gene of the CAR T cell may be further inactivated to avoid recipient's rejection of the donor's CART cell.

In some embodiments, the CAR comprises an antigen binding domain, a transmembrane domain, and an intracellular domain that may comprise a costimulatory signaling region and a CD3 zeta signaling domain. In certain embodiments, an antigen binding domain of the CAR binds FZD10, TSHR, PRLR, Muc17, GUCY2C, CD207, CD19, or CD20. In certain embodiments, a costimulatory signaling region of the CAR comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In some embodiments, the cell has a reduced graft-versus-host disease (GVHD) response in a biocompatible human recipient as compared to the GVHD response of the primary human T cell in a human subject in response to allogenic CART treatment.

In some embodiments, the isolated cell or the cell line is a T cell comprising a nucleic acid sequence encoding hTERT or a nucleic acid encoding SV40LT, or a combination thereof.

In some embodiments, the T cell comprises a nucleic acid sequence encoding hTERT and a nucleic acid encoding SV40LT. In some embodiments, expression of hTERT is regulated by an inducible expression system. In some embodiments, expression of SV40LT gene is regulated by an inducible expression system. In some embodiments, the inducible expression system is rTTA-TRE, which increases or activates the expression of SV40LT gene or hTERT gene, or a combination thereof. In some embodiments, the T cell comprises a nucleic acid sequence encoding a suicide gene. In some embodiments, the suicide gene is an HSV-TK system. Some embodiments relate to a method of treating cancer in a subject. The method may include administering a genetically modified cell to the subject, and the cancer is selected from the group consisting of a lung carcinoma, pancreatic cancer, liver cancer, bone cancer, breast cancer, colorectal cancer, leukemia, ovarian cancer, lymphoma, and brain cancer.

The term "Chimeric Antigen Receptor" or alternatively a "CAR" refers to a recombinant polypeptide construct comprising at least an extracellular antigen binding domain, a transmembrane domain and an intracellular signaling domain (e.g., cytoplasmic domain). In some embodiments, the domains of the CAR polypeptide construct are on the same polypeptide chain (e.g., comprising a chimeric fusion protein), and in some embodiments, the domains of the CAR polypeptide construct are not contiguous with each other (e.g., on different polypeptide chains).

In some embodiments, the intracellular signaling domain may include a functional signaling domain derived from a stimulatory molecule and/or a co-stimulatory molecule as described above. In certain embodiments, the intracellular signaling domain includes a functional signaling domain derived from a primary signaling domain (e.g., a primary signaling domain of CD3-zeta). In other embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may include up to 300 amino acids, preferably 10 to 100 amino acids, and most preferably 25 to 50 amino acids.

The extracellular domain of a CAR may include an antigen binding domain (e.g., a scFv, a single domain antibody (e.g. Fab), or TCR (e.g., a TCR alpha binding domain or TCR beta binding domain)) that targets a specific tumor marker (e.g., a tumor antigen). Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostate, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. For example, the tumor antigen is CD19, and the CAR thereof may be referred as CD19CAR.

In some embodiments, the extracellular domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID NO.: 44), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can, in turn, be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor a 2, IL-11 receptor a, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In some embodiments, the binding element of the CAR includes any antigen binding moiety that when bound to its cognate antigen, affects a tumor cell such that the tumor cell fails to grow, or is promoted to die or diminish.

The nucleic acid sequences coding for the desired molecules (e.g., CARs and ZFNs) can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors comprising a nucleic acid sequence described herein. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding CARs or ZFNs is typically achieved by operably linking a nucleic acid encoding the polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to the expression of synthetic nucleic acids encoding CARs and gene transfer into mammalian cells is provided in U.S. Pat. No. 8,906,682, incorporated by reference in its entirety.

Pharmaceutical compositions of the present disclosure are administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In certain embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the pharmaceutical compositions described herein may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection. In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In some embodiments, the cell compositions of the present disclosure are administered to a patient in conjunction with (e.g., before, simultaneously, or following) bone marrow transplantation, T cell ablative therapy using either chemotherapy agents such as, fludarabine, external-beam radiation therapy (XRT), cyclophosphamide, or antibodies such as OKT3 or CAMPATH. In other embodiments, the cell compositions of the present disclosure are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present disclosure. In other embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

Some embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances proliferation of CAR-expressing T cells.

In some embodiments, the sample is a cryopreserved sample. In some embodiments, the sample of cells is from umbilical cord blood or a peripheral blood sample from the subject. In some embodiments, the sample of cells is obtained by apheresis or venipuncture. In some embodiments, the sample of cells is a subpopulation of T cells.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

Exemplary Embodiments

The following are exemplary embodiments:
1. A zinc finger nuclease (ZFN) comprising: a first zinc finger protein (ZFP) that binds a first target site in a T-cell receptor alpha constant (TRAC) gene, the first ZFP comprising three or more zinc finger domains; a second ZFP that binds a second target site in the TRAC gene, the second ZFP comprising three or more zinc finger domains; and a cleavage domain, wherein: the first ZFP comprises amino acid sequences in the following order: SEQ ID NOS.: 2, 5-7, 2, and 19, and the second ZFP comprises amino acid sequences in the following order: SEQ ID NOS.: 2, 1-3, and 22; the first ZFP comprises amino acid sequences in the following order: SEQ ID NOS.: 2, 5-7, 2, and 19, and the second ZFP comprises amino acid sequences in the following order: SEQ ID NOS.: 1-3, and 22; the first ZFP comprises amino acid sequences in the following order: SEQ ID NOS.: 2, 5, 11, 7, 2, and 9, and the second ZFP comprises amino acid sequences in the following order: SEQ ID NOS.: 2, 1-3, and 22; the first ZFP comprises amino acid sequences in the following order: SEQ ID NOS.: 2, 5, 11, 7, 2, and 9, and the second ZFP comprises amino acid sequences in the following order: SEQ ID NOS.: 1-3, and 22; the first ZFP comprises amino acid sequences in the following order: SEQ ID NOS.: 2, 5, 15, 7, 2, and 9, and the second ZFP comprises amino acid sequences in the following order: SEQ ID NOS.: 2, 1-3 and 22; the first ZFP comprises amino acid sequences in the following order: SEQ ID NOS.: 2, 5, 15, 7, 2, and 9, and the second ZFP comprises amino acid sequences in the following order: SEQ ID NOS.: 1-3, 22; or the first ZFP comprises amino acid sequences in the following order: SEQ ID NOS.: 2, 5, 23, and 7, 2, and 9, and the second ZFP comprises amino acid sequences in the following order: SEQ ID NOS.: 1-3, 22; and wherein the amino acid sequences of the ZFPs are ordered from the N-terminus to the C-terminus of the respective ZFP.
2. An ZFN comprising: a first zinc finger protein (ZFP) that binds a first target site in a T-cell receptor alpha constant (TRAC) gene, the first ZFP comprising three or more zinc finger domains; a second ZFP that binds a second target site in the TRAC gene, the second ZFP comprising three or more zinc finger domains; and a cleavage domain, wherein: the first ZFP is ZFL-5, and the second ZFP is ZFR-4; the first ZFP is ZFL-5, and the second ZFP is ZFR-3; the first ZFP is ZFL-4, and the second ZFP is ZFR-4; the first ZFP is ZFLm1, and the second ZFP is ZFRm1; the first ZFP is ZFLm1, and the second ZFP is ZFRm1-4; the first ZFP is ZFLm1, and the second ZFP is ZFRm1-3; the first ZFP is ZFLm1-5, and the second ZFP is ZFRm1; the first ZFP is ZFLm1-5, and the second ZFP is ZFRm1-4; the first ZFP is ZFLm1-4, and the second ZFP is ZFRm1; the first ZFP is ZFLm1-4, and the second ZFP is ZFRm1-4; the first ZFP is ZFLm2, and the second ZFP is ZFRm1; the first ZFP is ZFLm2, and the second ZFP is ZFRm1-4; the first ZFP is ZFLm2, and the second ZFP is ZFRm1-3; the first ZFP is ZFLm2-5, and the second ZFP is ZFRm1; the first ZFP is ZFLm2-5, and the second ZFP is ZFRm1-4; the first ZFP is ZFLm2-4, and the second ZFP is ZFRm1; the first ZFP is ZFLm2-4, and the second ZFP is ZFRm1-4; the first ZFP is ZFLm3, and the second ZFP is ZFRm1; the first ZFP is ZFLm3, and the second ZFP is ZFRm1-4; the first ZFP is ZFLm3, and the second ZFP is ZFRm1-3; the first ZFP is ZFLm3-5, and the second ZFP is ZFRm1-4; the first ZFP is ZFLm3-4, and the second ZFP is ZFRm1; the first ZFP is ZFLm4, and the second ZFP is ZFRm1; the first ZFP is ZFLm4, and the second ZFP is ZFRm1-4; the first ZFP is ZFLm4, and the second ZFP is ZFRm1-3; or the first ZFP is ZFLm4-4, and the second ZFP is ZFRm1-4; and wherein the ZFPs are described in Table 1.
3. An ZFN comprising: a first ZFP that binds a first target site in a TRAC gene; a second ZFP that binds a second target site in the TRAC gene; and a cleavage domain, wherein: the first target site comprises a nucleic acid sequence SEQ ID NO.: 13, and the second target site comprises a nucleic acid sequence SEQ ID NO.: 10; the first target site comprises a nucleic acid sequence SEQ ID NO.: 13, and the second target site comprises a nucleic acid sequence SEQ ID NO.: 43 (GACTTTGCA); the first target site comprises a nucleic acid sequence SEQ ID NO.: 14, and the second target site comprises a nucleic acid sequence SEQ ID NO.: 10; the first target site comprises a nucleic acid sequence SEQ ID NO.: 20, and the second target site comprises a nucleic acid sequence SEQ ID NO.: 10; the first target site comprises a nucleic acid sequence SEQ ID NO.: 20, and the second target site comprises a nucleic acid sequence SEQ ID NO.: 43 (GACTTTGCA); the first target site comprises a nucleic acid sequence SEQ ID NO.: 13, and the second target site comprises a nucleic acid sequence SEQ ID NO.: 21; the first target site comprises a nucleic acid sequence SEQ ID NO.: 13, and the second target site comprises a nucleic acid sequence SEQ ID NO.: 10; the first target site comprises a nucleic acid sequence SEQ ID NO.: 14, and the second target site comprises a nucleic acid sequence SEQ ID NO.: 21; the first target site comprises a nucleic acid sequence SEQ ID NO.: 14, and the second target site comprises a nucleic acid sequence SEQ ID NO.: 10; the first target site comprises a nucleic acid sequence SEQ ID NO.: 20, and the second target site comprises an nucleic acid sequence SEQ ID NO.: 10; the first target site comprises a nucleic acid sequence SEQ ID NO.: 20, and the second target site comprises a nucleic acid sequence SEQ ID NO.: 43 (GACTTTGCA); the first target site comprises a nucleic acid sequence SEQ ID NO.: 13, and the second target site comprises a nucleic acid sequence SEQ ID NO.: 21; the first target site comprises a nucleic acid sequence SEQ ID NO.: 13, and the second target site comprises a nucleic acid sequence SEQ ID NO.: 10; the first target site comprises a nucleic acid sequence SEQ ID NO.: 14, and the second target site comprises a nucleic acid sequence SEQ ID NO.: 21; the first target site comprises a nucleic acid sequence SEQ ID NO.: 14, and the second target site comprises a nucleic acid sequence SEQ ID NO.: 10; the first target site comprises a nucleic acid sequence SEQ ID NO.: 20, and the second target site comprises an nucleic acid sequence SEQ ID NO.: 10; the first target site comprises a nucleic acid sequence SEQ ID NO.: 20, and the second target site comprises a nucleic acid sequence SEQ ID NO.: 43 (GACTTTGCA); the first target site comprises a nucleic acid sequence SEQ ID NO.: 13, and the second target site comprises a nucleic acid sequence SEQ ID NO.: 10; the first target site comprises a nucleic acid sequence SEQ ID NO.: 14, and the second target site comprises a nucleic acid sequence SEQ ID NO.: 21; the first target site comprises a nucleic acid sequence SEQ ID NO.: 20, and the second target site comprises a nucleic acid sequence SEQ ID NO.: 43 (GACTTTGCA); or the first target site comprises a nucleic acid sequence SEQ ID NO.: 14, and the second target site comprises a nucleic acid sequence SEQ ID NO.: 10.

4. The ZFN of any one of embodiments 1-3, wherein the TRAC gene is a human TRAC gene.

5. The ZFN of any one of embodiments 1-3, wherein the cleavage domain comprises a wild-type or engineered FokI cleavage domain.

6. A polynucleotide encoding the ZFN of any one of embodiments 1-3.

7. A vector comprising the polynucleotide of embodiment 6.

8. The vector of embodiment 7, wherein the vector is an adenoviral or lentiviral vector.

9. A cell or a cell line comprising the ZFN of any of embodiments 1-3.

10. The cell or the cell line of embodiment 9, wherein the cell is a stem cell, a T cell or a Natural Killer (NK) cell.

11. The cell or the cell line of embodiment 9, wherein the cell is a T cell derived from a primary human T cell isolated from a human donor.

12. The cell or the cell line of embodiment 11, wherein the cell has a reduced expression of endogenous TRAC gene.

13. A cell comprising a nucleic acid sequence encoding a chimeric antigen receptor (CAR), wherein the TRAC gene is inactivated using the ZFN of any of embodiments 1-3.

14. The cell or the cell line of embodiment 13, wherein the CAR comprises an antigen binding domain, a transmembrane domain, a costimulatory signaling region, and a CD3 zeta signaling domain.

15. The cell or the cell line of embodiment 13, wherein the cell has a reduced graft-versus-host disease (GVHD) response in a bioincompatible human recipient as compared to the GVHD response of the primary human T cell in a human subject in response to allogenic CAR T treatment.

16. The isolated cell or the cell line of embodiment 13, wherein an antigen binding domain of the CAR binds FZD10, TSHR, PRLR, Muc17, GUCY2C, CD207, CD19, or CD20.

17. The cell or the cell line of embodiment 13, wherein a costimulatory signaling region of the CAR comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

18. The cell or the cell line of embodiment 11, wherein the cell or the cell line is a T cell comprising a nucleic acid sequence encoding hTERT or a nucleic acid encoding SV40LT, or a combination thereof.

19. The cell or the cell line of embodiment 18, wherein the T cell comprises a nucleic acid sequence encoding hTERT and a nucleic acid encoding SV40LT.

20. The cell or the cell line of embodiment 18, wherein expression of hTERT is regulated by an inducible expression system.

21. The cell or the cell line of embodiment 18, wherein expression of SV40LT gene is regulated by an inducible expression system.

22. The cell or the cell line of embodiment 21, wherein the inducible expression system is rTTA-TRE, which activates the expression of SV40LT gene or hTERT gene, or a combination thereof.

23. The cell or the cell line of embodiment 18, wherein the T cell comprises a nucleic acid sequence encoding a suicide gene.

24. The cell or the cell line of embodiment 23, wherein the suicide gene is an HSV-TK system.

25. A method of treating cancer in a subject, the method comprising: administering a genetically modified cell of embodiment 13 to the subject, wherein the cancer is selected from the group consisting of a lung carcinoma, pancreatic cancer, liver cancer, bone cancer, breast cancer, colorectal cancer, leukemia, ovarian cancer, lymphoma, and brain cancer.

26. The ZFN of embodiment 1, wherein a percentage of cells introduced with the ZFN of embodiment 1 and having ZFN mediated gene modification is more than 20.

Example 1. Design of TRAC-Specific ZFNs

TRAC-specific ZFNs were constructed to enable the site-specific introduction of mutations at TRAC gene (FIG. 1). Various ZFNs were designed and incorporated into plasmids vectors essentially as described in Urnov et al. (2005) Nature 435(7042):646-65252, Lombardo et al. (2007) Nat Biotechnol. November; 25(11):1298-306, and U.S. Patent Publication 2008/0131962. The ZFNs include various of combinations of Zinc finger proteins (e.g., ZFN-left and ZFN-right binding protein), which are listed in Table 1. The cleavage domain of the ZFNs comprised an engineered FokI cleavage domain (SEQ ID NOS.: 17, or 18).

TABLE 1

Exemplary ZFNs and their target sequences

| IDs of Zinc finger DNA binding protein Right (SEQ ID NO:) | Target Sequence of TRAC gene (SEQ ID NO:) | F1 (SEQ ID NO:) | F2 (SEQ ID NO:) | F3 (SEQ ID NO:) | F4 (SEQ ID NO:) | F5 (SEQ ID NO:) | F6 (SEQ ID NO:) |
|---|---|---|---|---|---|---|---|
| ZFR (Right arm of Zinc Finger Protein) | 21 | 2 | 1 | 2 | 3 | 4 | |
| ZFR-4 | 10 | 1 | 2 | 3 | 4 | | |
| ZFR-3 | 43 (GACTTTGCA) | 2 | 3 | 4 | | | |
| ZFRm1 | 21 | 2 | 1 | 2 | 3 | 22 | |
| ZFRm1-4 | 10 | 1 | 2 | 3 | 22 | | |
| ZFRm1-3 | 43 (GACTTTGCA) | 2 | 3 | 22 | | | |
| ZFRm2 | 21 | 2 | 1 | 24 | 3 | 4 | |
| ZFRm2-4 | 10 | 1 | 24 | 3 | 4 | | |
| ZFRm2-3 | 43 (GACTTTGCA) | 24 | 3 | 4 | | | |

| IDs of Zinc finger DNA binding protein Left (SEQ ID NO:) | Target Sequence of TRAC gene (SEQ ID NO:) | F1 (SEQ ID NO:) | F2 (SEQ ID NO:) | F3 (SEQ ID NO:) | F4 (SEQ ID NO:) | F5 (SEQ ID NO:) | F6 (SEQ ID NO:) |
|---|---|---|---|---|---|---|---|
| ZFL (Left arm of Zinc Finger Protein) | 20 | 2 | 5 | 6 | 7 | 2 | 9 |
| ZFL-5 | 13 | 5 | 6 | 7 | 2 | 9 | |
| ZFL-4 | 14 | 6 | 7 | 2 | 9 | | |
| ZFLm1 | 20 | 2 | 5 | 6 | 7 | 2 | 19 |
| ZFL-3 | 16 | 7 | 2 | 9 | | | |
| ZFLm1-5 | 13 | 5 | 6 | 7 | 2 | 19 | |
| ZFLm1-4 | 14 | 6 | 7 | 2 | 19 | | |
| ZFLm1-3 | 16 | 7 | 2 | 19 | | | |
| ZFLm2 | 20 | 2 | 5 | 11 | 7 | 2 | 9 |
| ZFLm2-5 | 13 | 5 | 11 | 7 | 2 | 9 | |
| ZFLm2-4 | 14 | 11 | 7 | 2 | 9 | | |
| ZFLm3 | 20 | 2 | 5 | 15 | 7 | 2 | 9 |
| ZFLm3-5 | 13 | 5 | 15 | 7 | 2 | 9 | |
| ZFLm3-4 | 14 | 15 | 7 | 2 | 9 | | |

TABLE 1-continued

Exemplary ZFNs and their target sequences

| ZFLm4 | 20 | 2 | 5 | 23 | 7 | 2 | 9 |
|---|---|---|---|---|---|---|---|
| ZFLm4-5 | 43 (GACTTTGCA) | | 5 | 23 | 7 | 2 | 9 |
| ZFLm4-4 | 14 | | | 23 | 7 | 2 | 9 |

Example 2. ZFN Activity In Vitro

ZFN-left (ZFL) arm plasmid vectors and ZFN-right (ZFR) arm plasmid vectors were transfected into Hela cells using fugene transfection reagent, respectively. After transfection of 24 hours, Hela cells were treated with 1 μg/ml puromycin for 48 hours to obtain cells rich in ZFNs. The Hela cells were then collected, and lysed DNA fragment containing ZFNs were amplified by PCR using primers specific to TRAC gene and the genome of Hela cells as templates. The DNA fragments were sequenced using forward primers, and the sequencing results are shown in FIG. 2-8.

The DNA fragments were cloned into vectors. The DNA fragments of about 30 monoclonal cells were sequenced to determine whether the DNA fragments include mutations. The results of the sequencing were shown in Table 2.

TABLE 2

Sequencing results for ZFNs from monoclonal cells that target TRAC gene fragments and are amplified by PCR

| ZFN Left | ZFN Right | Presence of Double sequencing signals | Number of clones analyzed | Number of clones mutated | percentage of mutation |
|---|---|---|---|---|---|
| ZFL | ZFR | YES | 36 | 10 | 28% |
| ZFL-5 | ZFR-4 | YES | 29 | 4 | 14% |
| ZFL-5 | ZFR-3 | YES | 30 | 1 | 3% |
| ZFL-4 | ZFR-4 | YES | 31 | 2 | 6% |
| ZFL-4 | ZFR-3 | YES | 30 | 0 | 0% |
| ZFL-3 | ZFR-4 | YES | 30 | 0 | 0% |
| ZFL-3 | ZFR-3 | YES | 30 | 0 | 0% |
| ZFLm1 | ZFRm1 | YES | 37 | 11 | 30% |
| ZFLm1 | ZFRm1-4 | YES | 37 | 18 | 49% |
| ZFLm1 | ZFRm1-3 | YES | 28 | 5 | 18% |
| ZFLm1-5 | ZFRm1 | YES | 30 | 1 | 3% |
| ZFLm1-5 | ZFRm1-4 | YES | 29 | 1 | 3% |
| ZFLm1-5 | ZFRm1-3 | NONE | 30 | 0 | 0% |
| ZFLm1-4 | ZFRm1 | YES | 29 | 1 | 3% |
| ZFLm1-4 | ZFRm1-4 | YES | 31 | 3 | 10% |
| ZFLm1-4 | ZFRm1-3 | NONE | 30 | 0 | 0% |
| ZFLm1-3 | ZFRm1 | NONE | 30 | 0 | 0% |
| ZFLm1-3 | ZFRm1-4 | NONE | 30 | 0 | 0% |
| ZFLm1-3 | ZFRm1-3 | NONE | 30 | 0 | 0% |
| ZFLm2 | ZFRm1 | YES | 28 | 8 | 29% |
| ZFLm2 | ZFRm1-4 | YES | 32 | 7 | 22% |
| ZFLm2 | ZFRm1-3 | YES | 28 | 2 | 7% |
| ZFLm2-5 | ZFRm1 | YES | 31 | 2 | 6% |
| ZFLm2-5 | ZFRm1-4 | YES | 32 | 2 | 6% |
| ZFLm2-5 | ZFRm1-3 | NONE | 30 | 0 | 0% |
| ZFLm2-4 | ZFRm1 | YES | 29 | 2 | 7% |
| ZFLm2-4 | ZFRm1-4 | YES | 30 | 1 | 3% |
| ZFLm2-4 | ZFRm1-3 | NONE | 30 | 0 | 0% |
| ZFLm2-3 | ZFRm1 | NONE | 30 | 0 | 0% |
| ZFLm2-3 | ZFRm1-4 | NONE | 30 | 0 | 0% |
| ZFLm2-3 | ZFRm1-3 | NONE | 30 | 0 | 0% |
| ZFLm3 | ZFRm1 | YES | 30 | 6 | 20% |
| ZFLm3 | ZFRm1-4 | YES | 38 | 10 | 26% |
| ZFLm3 | ZFRm1-3 | YES | 32 | 3 | 9% |
| ZFLm3-5 | ZFRm1 | NONE | 30 | 0 | 0% |
| ZFLm3-5 | ZFRm1-4 | YES | 29 | 2 | 7% |
| ZFLm3-5 | ZFRm1-3 | NONE | 30 | 0 | 0% |
| ZFLm3-4 | ZFRm1 | YES | 32 | 4 | 13% |
| ZFLm3-4 | ZFRm1-4 | NONE | 30 | 0 | 0% |
| ZFLm3-4 | ZFRm1-3 | NONE | 30 | 0 | 0% |
| ZFLm4 | ZFRm1 | YES | 28 | 4 | 14% |
| ZFLm4 | ZFRm1-4 | YES | 34 | 8 | 24% |
| ZFLm4 | ZFRm1-3 | YES | 31 | 5 | 16% |
| ZFLm4-5 | ZFRm1 | NONE | 30 | 0 | 0% |
| ZFLm4-5 | ZFRm1-4 | YES | 30 | 0 | 0% |
| ZFLm4-5 | ZFRm1-3 | NONE | 30 | 0 | 0% |
| ZFLm4-4 | ZFRm1 | NONE | 30 | 0 | 0% |
| ZFLm4-4 | ZFRm1-4 | YES | 34 | 5 | 15% |
| ZFLm4-4 | ZFRm1-3 | NONE | 30 | 0 | 0% |

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

What is claimed is:

1. A modified cell comprising a zinc finger nuclease (ZFN) comprising: a first zinc finger protein (ZFP) that binds a first target site in a T cell receptor alpha constant (TRAC) gene; a second ZFP that binds a second target site in the TRAC gene; and a cleavage domain, wherein
- the first target site comprises nucleic acid sequence SEQ ID NO: 13, and the second target site comprises nucleic acid sequence SEQ ID NO: 10;
- the first target site comprises nucleic acid sequence SEQ ID NO: 13, and the second target site comprises nucleic acid sequence SEQ ID NO: 43;
- the first target site comprises nucleic acid sequence SEQ ID NO: 14, and the second target site comprises a nucleic acid sequence SEQ ID NO: 10;
- the first target site comprises nucleic acid sequence SEQ ID NO: 20, and the second target site comprises nucleic acid sequence SEQ ID NO: 10;
- the first target site comprises nucleic acid sequence SEQ ID NO: 20, and the second target site comprises a nucleic acid sequence SEQ ID NO: 43;
- the first target site comprises nucleic acid sequence SEQ ID NO: 13, and the second target site comprises nucleic acid sequence SEQ ID NO: 21; or
- the first target site comprises nucleic acid sequence SEQ ID NO: 14, and the second target site comprises nucleic acid sequence SEQ ID NO: 21; and
- wherein the genetically modified cell has a reduced expression of endogenous TRAC gene.

2. The modified cell of claim 1, wherein the first target site comprises nucleic acid sequence SEQ ID NO: 13, and the second target site comprises nucleic acid sequence SEQ ID NO: 10.

3. The modified cell of claim 1, wherein the first target site comprises nucleic acid sequence SEQ ID NO.: 13, and the second target site comprises nucleic acid sequence SEQ ID NO: 43.

4. The modified cell of claim 1, wherein the first target site comprises nucleic acid sequence SEQ ID NO.: 14, and the second target site comprises nucleic acid sequence SEQ ID NO: 10.

5. The modified cell of claim 1, wherein the first target site comprises nucleic acid sequence SEQ ID NO: 20, and the second target site comprises nucleic acid sequence SEQ ID NO: 10.

6. The modified cell of claim 1, wherein the first target site comprises nucleic acid sequence SEQ ID NO: 20, and the second target site comprises nucleic acid sequence SEQ ID NO: 43.

7. The modified cell of claim 1, wherein the first target site comprises nucleic acid sequence SEQ ID NO: 13, and the second target site comprises nucleic acid sequence SEQ ID NO: 21.

8. The modified cell of claim 1, wherein the first target site comprises nucleic acid sequence SEQ ID NO: 14, and the second target site comprises nucleic acid sequence SEQ ID NO: 21.

9. The modified cell of claim 1, wherein the TRAC gene is a human TRAC gene.

10. The modified cell of claim 1, wherein the cleavage domain comprises a wild-type or engineered FokI cleavage domain.

11. The modified cell of claim 1, wherein the modified cell is a stem cell, a T cell, or a Natural Killer (NK) cell.

12. The modified cell of claim 1, wherein the modified cell is a T cell derived from a primary human T cell from a human donor.

13. The modified cell of claim 1, wherein the modified cell further comprises a nucleic acid encoding a chimeric antigen receptor (CAR).

14. The modified cell of claim 13, wherein the TRAC gene is inactivated using the ZFN of claim 1.

15. The modified cell of claim 13, wherein the CAR comprises an antigen binding domain, a transmembrane domain, a costimulatory signaling region, and a CD3 zeta signaling domain.

16. The modified cell of claim 13, wherein the modified cell has a reduced graft-versus-host disease (GVHD) response in a bioincompatible human recipient as compared to the GVHD response of the primary human T cell in response to allogenic CAR T treatment.

17. The modified cell of claim 13, wherein an antigen binding domain of the CAR binds FZD10, TSHR, PRLR, Muc17, GUCY2C, CD207, CD19, or CD20.

18. The modified cell of claim 13, wherein an antigen binding domain of the CAR binds a tumor antigen of a solid tumor.

19. The modified cell of claim 13, wherein a costimulatory signaling region of the CAR comprises an intracellular domain of a costimulatory molecule comprising CD27, CD28, 4-1BB, OX40, CD30, CD40, PD-1, ICOS, lymphocyte function-associated antigen-1 (LFA-1), CD2, CD7, LIGHT, NKG2C, B7-H3, or any combination thereof.

20. The modified cell of claim 1, wherein the modified cell is a T cell comprising a nucleic acid encoding hTERT or a nucleic acid encoding SV40LT, or a combination thereof.

21. A composition comprising the modified cells of claim 1.

22. A method of treating a subject with cancer, the method comprising administering an effective amount of the composition of claim 21 to the subject.

\* \* \* \* \*

SEQUENCE LISTING

<160> NUMBER OF SEQ ID NOS: 46

<210> SEQ ID NO 1
<211> LENGTH: 7
<212> TYPE: PRT
<213> ORGANISM: Artificial Sequence
<220> FEATURE:
<223> OTHER INFORMATION: Synthesized

<400> SEQUENCE: 1

Trp Arg Ser Ser Leu Ala Ser
1               5

<210> SEQ ID NO 2
<211> LENGTH: 7

```
<212> TYPE: PRT
<213> ORGANISM: Artificial Sequence
<220> FEATURE:
<223> OTHER INFORMATION: Synthesized

<400> SEQUENCE: 2

Gln Ser Gly Asp Leu Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Synthesized

<400> SEQUENCE: 3

His Lys Trp Val Leu Arg Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Synthesized

<400> SEQUENCE: 4

Asp Arg Ser Asn Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthesized

<400> SEQUENCE: 5

Gln Trp Gly Thr Arg Tyr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthesized

<400> SEQUENCE: 6

Glu Arg Gly Thr Leu Ala Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthesized

<400> SEQUENCE: 7

Arg Ser Asp Asn Leu Arg Glu
1               5

<210> SEQ ID NO 8
<211> LENGTH: 196
<212> TYPE: PRT
```

<213> ORGANISM: Artificial Sequence
<220> FEATURE:
<223> OTHER INFORMATION: Synthesized

<400> SEQUENCE: 8

```
Gln Leu Val Lys Ser Glu Leu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195
```

<210> SEQ ID NO 9
<211> LENGTH: 7
<212> TYPE: PRT
<213> ORGANISM: Artificial Sequence
<220> FEATURE:
<223> OTHER INFORMATION: Synthesized

<400> SEQUENCE: 9

```
Thr Ser Gly Ser Leu Thr Arg
1               5
```

<210> SEQ ID NO 10
<211> LENGTH: 12
<212> TYPE: DNA
<213> ORGANISM: Artificial Sequence
<220> FEATURE:
<223> OTHER INFORMATION: Synthesized

<400> SEQUENCE: 10
gactttgcat gt                                                          12

<210> SEQ ID NO 11
<211> LENGTH: 7
<212> TYPE: PRT
<213> ORGANISM: Artificial Sequence
<220> FEATURE:
<223> OTHER INFORMATION: Synthesized

<400> SEQUENCE: 11

Asp Lys Ser Cys Leu Asn Arg
1               5

<210> SEQ ID NO 12
<211> LENGTH: 18
<212> TYPE: DNA
<213> ORGANISM: Artificial Sequence
<220> FEATURE:
<223> OTHER INFORMATION: Synthesized

<400> SEQUENCE: 12
gactttgcag actttgca                                                    18

<210> SEQ ID NO 13
<211> LENGTH: 16
<212> TYPE: DNA
<213> ORGANISM: Artificial Sequence
<220> FEATURE:
<223> OTHER INFORMATION: Synthesized

<400> SEQUENCE: 13
gttgctccag gccaca                                                      16

<210> SEQ ID NO 14
<211> LENGTH: 13
<212> TYPE: DNA
<213> ORGANISM: Artificial Sequence
<220> FEATURE:
<223> OTHER INFORMATION: Synthesized

<400> SEQUENCE: 14
gttgctccag gcc                                                         13

<210> SEQ ID NO 15
<211> LENGTH: 7
<212> TYPE: PRT
<213> ORGANISM: Artificial Sequence
<220> FEATURE:
<223> OTHER INFORMATION: Synthesized

<400> SEQUENCE: 15

Asp Cys Arg Asp Leu Ala Arg
1               5

<210> SEQ ID NO 16
<211> LENGTH: 10
<212> TYPE: DNA
<213> ORGANISM: Artificial Sequence
<220> FEATURE:
<223> OTHER INFORMATION: Synthesized

<400> SEQUENCE: 16
gttgctccag                                                             10

<210> SEQ ID NO 17
<211> LENGTH: 196
<212> TYPE: PRT
<213> ORGANISM: Artificial Sequence
<220> FEATURE:
<223> OTHER INFORMATION: Synthesized

<400> SEQUENCE: 17

Gln Leu Val Lys Ser Glu Leu Glu Lys Lys Ser Glu Leu Arg His
1               5                   10                  15

Lys Leu Lys Tyr Val Pro His Glu Tyr Ile Glu Leu Ile Glu Ile Ala

```
                    20                  25                  30
Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 18
<211> LENGTH: 196
<212> TYPE: PRT
<213> ORGANISM: Artificial Sequence
<220> FEATURE:
<223> OTHER INFORMATION: Synthesized

<400> SEQUENCE: 18

Gln Leu Val Lys Ser Glu Leu Glu Glu Lys Lys Ser Glu Leu Arg His
 1               5                  10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
```

Glu Ile Asn Phe
        195

<210> SEQ ID NO 19
<211> LENGTH: 7
<212> TYPE: PRT
<213> ORGANISM: Artificial Sequence
<220> FEATURE:
<223> OTHER INFORMATION: Synthesized

<400> SEQUENCE: 19

Thr Ser Gly Ala Leu Thr Arg
1               5

<210> SEQ ID NO 20
<211> LENGTH: 19
<212> TYPE: DNA
<213> ORGANISM: Artificial Sequence
<220> FEATURE:
<223> OTHER INFORMATION: Synthesized

<400> SEQUENCE: 20
gttgctccag gccacagca                                        19

<210> SEQ ID NO 21
<211> LENGTH: 15
<212> TYPE: DNA
<213> ORGANISM: Artificial Sequence
<220> FEATURE:
<223> OTHER INFORMATION: Synthesized

<400> SEQUENCE: 21
gactttgcat gtgca                                            15

<210> SEQ ID NO 22
<211> LENGTH: 7
<212> TYPE: PRT
<213> ORGANISM: Artificial Sequence
<220> FEATURE:
<223> OTHER INFORMATION: Synthesized

<400> SEQUENCE: 22

Cys Pro Ser Asn Leu Arg Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthesized

<400> SEQUENCE: 23

Asp Arg Ser Asp Leu Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Synthesized

<400> SEQUENCE: 24

Gln Ser Gly Ser Leu Thr Arg

<210> SEQ ID NO 25
<211> LENGTH: 21
<212> TYPE: PRT
<213> ORGANISM: Artificial Sequence
<220> FEATURE:
<223> OTHER INFORMATION: Synthesized

<400> SEQUENCE: 25

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 26
<211> LENGTH: 69
<212> TYPE: PRT
<213> ORGANISM: Artificial Sequence
<220> FEATURE:
<223> OTHER INFORMATION: Synthesized

<400> SEQUENCE: 26

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65
```

<210> SEQ ID NO 27
<211> LENGTH: 42
<212> TYPE: PRT
<213> ORGANISM: Artificial Sequence
<220> FEATURE:
<223> OTHER INFORMATION: Synthesized

<400> SEQUENCE: 27

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 28
<211> LENGTH: 112
<212> TYPE: PRT
<213> ORGANISM: Artificial Sequence
<220> FEATURE:
<223> OTHER INFORMATION: Synthesized

<400> SEQUENCE: 28

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
```

```
            35                  40                  45
Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 29
<211> LENGTH: 242
<212> TYPE: PRT
<213> ORGANISM: Artificial Sequence
<220> FEATURE:
<223> OTHER INFORMATION: Synthesized

<400> SEQUENCE: 29

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Lys Tyr
                 20                  25                  30

Leu Asn Trp Tyr Gln Gln Lys Pro Gly Lys Ala Pro Lys Leu Leu Ile
             35                  40                  45

Tyr His Thr Ser Arg Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
                180                 185                 190

Arg Asp Asn Ala Lys Asn Ser Leu Tyr Leu Gln Met Asn Ser Leu Arg
                195                 200                 205

Ala Glu Asp Thr Ala Val Tyr Tyr Cys Ala Lys His Tyr Tyr Tyr Gly
            210                 215                 220

Gly Ser Tyr Ala Met Asp Tyr Trp Gly Gln Gly Thr Leu Val Thr Val
225                 230                 235                 240

Ser Ser

<210> SEQ ID NO 30
<211> LENGTH: 242
<212> TYPE: PRT
<213> ORGANISM: Artificial Sequence
<220> FEATURE:
<223> OTHER INFORMATION: Synthesized
```

<400> SEQUENCE: 30

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Lys Tyr
            20                  25                  30
Leu Asn Trp Tyr Gln Gln Lys Pro Asp Gly Thr Val Lys Leu Leu Ile
        35                  40                  45
Tyr His Thr Ser Arg Leu His Ser Gly Val Pro Ser Arg Phe Ser Gly
    50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asn Thr Leu Pro Tyr
                85                  90                  95
Thr Phe Gly Gly Gly Thr Lys Leu Glu Ile Thr Gly Gly Gly Gly Ser
            100                 105                 110
Gly Gly Gly Gly Ser Gly Gly Gly Ser Glu Val Lys Leu Gln Glu
        115                 120                 125
Ser Gly Pro Gly Leu Val Ala Pro Ser Gln Ser Leu Ser Val Thr Cys
130                 135                 140
Thr Val Ser Gly Val Ser Leu Pro Asp Tyr Gly Val Ser Trp Ile Arg
145                 150                 155                 160
Gln Pro Pro Arg Lys Gly Leu Glu Trp Leu Gly Val Ile Trp Gly Ser
                165                 170                 175
Glu Thr Thr Tyr Tyr Asn Ser Ala Leu Lys Ser Arg Leu Thr Ile Ile
            180                 185                 190
Lys Asp Asn Ser Lys Ser Gln Val Phe Leu Lys Met Asn Ser Leu Gln
        195                 200                 205
Thr Asp Asp Thr Ala Ile Tyr Tyr Cys Ala Lys His Tyr Tyr Tyr Gly
    210                 215                 220
Gly Ser Tyr Ala Met Asp Tyr Trp Gly Gln Gly Thr Ser Val Thr Val
225                 230                 235                 240
Ser Ser
```

<210> SEQ ID NO 31
<211> LENGTH: 237
<212> TYPE: PRT
<213> ORGANISM: Artificial Sequence
<220> FEATURE:
<223> OTHER INFORMATION: Synthesized

<400> SEQUENCE: 31

```
Asp Ile Gln Met Thr Gln Ser Pro Ala Ser Leu Ser Val Ser Val Gly
1               5                   10                  15
Glu Thr Val Thr Ile Thr Cys Arg Ala Ser Glu Asn Ile Tyr Ser Asn
            20                  25                  30
Leu Ala Trp Tyr Gln Gln Lys Gln Gly Lys Ser Pro Gln Leu Leu Val
        35                  40                  45
Tyr Val Ala Thr Asn Leu Ala Asp Gly Val Pro Ser Arg Phe Ser Gly
    50                  55                  60
Ser Gly Ser Gly Thr Gln Tyr Ser Leu Lys Ile Asn Ser Leu Gln Ser
65                  70                  75                  80
Glu Asp Phe Gly Ser Tyr Tyr Cys Gln His Phe Trp Gly Thr Pro Tyr
                85                  90                  95
Thr Phe Gly Gly Gly Thr Lys Leu Gly Gly Gly Gly Ser Gly Gly Gly
            100                 105                 110
```

Gly Ser Gly Gly Gly Ser Glu Val Gln Leu Gln Gln Ser Gly Ala
            115                 120                 125

Glu Leu Val Lys Pro Gly Ala Ser Val Lys Leu Ser Cys Thr Ala Ser
130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
            195                 200                 205

Asp Thr Ala Val Tyr Tyr Cys Ala Arg Gly Ala Arg Gly Ser Arg Phe
210                 215                 220

Ala Tyr Trp Gly Gln Gly Thr Leu Val Thr Val Ser Ala
225                 230                 235

<210> SEQ ID NO 32
<211> LENGTH: 244
<212> TYPE: PRT
<213> ORGANISM: Artificial Sequence
<220> FEATURE:
<223> OTHER INFORMATION: Synthesized

<400> SEQUENCE: 32

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Gly Ser Glu Val Gln
        115                 120                 125

Leu Val Gln Ser Gly Ala Glu Val Lys Lys Pro Gly Gln Ser Leu Lys
130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 33
<211> LENGTH: 252
<212> TYPE: PRT
<213> ORGANISM: Artificial Sequence
<220> FEATURE:
<223> OTHER INFORMATION: Synthesized

<400> SEQUENCE: 33

Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
        115                 120                 125

Glu Val Gln Leu Val Glu Ser Gly Gly Asp Leu Val Lys Pro Gly Gly
    130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
            180                 185                 190

Lys Gly Arg Phe Thr Ile Ser Arg Asp Asn Ala Lys Asn Thr Leu Tyr
        195                 200                 205

Leu Gln Met Ser Ser Leu Lys Ser Glu Asp Ser Ala Met Tyr Tyr Cys
    210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250

<210> SEQ ID NO 34
<211> LENGTH: 243
<212> TYPE: PRT
<213> ORGANISM: Artificial Sequence
<220> FEATURE:
<223> OTHER INFORMATION: Synthesized

<400> SEQUENCE: 34

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

```
Tyr Ser Gly Ser Thr Leu Gln Ser Gly Ile Pro Ser Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His His Glu Tyr Pro Tyr
                 85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Gln Val Gln Leu Gln Gln
            115                 120                 125

Pro Gly Ala Glu Leu Val Arg Pro Gly Ala Ser Val Lys Leu Ser Cys
130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
                180                 185                 190

Thr Val Asp Lys Ser Ser Ser Thr Ala Tyr Met Gln Leu Ser Ser Leu
            195                 200                 205

Thr Ser Glu Asp Ser Ala Val Tyr Tyr Cys Ala Arg Gly Pro Tyr Tyr
210                 215                 220

Gly Thr Asn Pro Trp Phe Pro Tyr Trp Gly Gln Gly Thr Leu Val Thr
225                 230                 235                 240

Val Ser Ser

<210> SEQ ID NO 35
<211> LENGTH: 241
<212> TYPE: PRT
<213> ORGANISM: Artificial Sequence
<220> FEATURE:
<223> OTHER INFORMATION: Synthesized

<400> SEQUENCE: 35

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Arg Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Gly Ser Leu Gln Ser
 65                  70                  75                  80

Glu Asp Phe Ala Val Tyr Tyr Cys Gln Gln Tyr Lys Thr Trp Pro Arg
                 85                  90                  95

Thr Phe Gly Gln Gly Thr Asn Val Glu Ile Lys Gly Gly Gly Gly Ser
                100                 105                 110

Gly Gly Gly Gly Ser Gly Gly Gly Gly Ser Gln Val Gln Leu Gln Gln
            115                 120                 125

Trp Gly Ala Gly Leu Leu Lys Pro Ser Glu Thr Leu Ser Leu Thr Cys
130                 135                 140

Ala Val Phe Gly Gly Ser Phe Ser Gly Tyr Tyr Trp Ser Trp Ile Arg
145                 150                 155                 160
```

-continued

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Phe Asp His Trp Gly Gln Gly Thr Leu Val Thr Val Ser
225                 230                 235                 240

Ser

<210> SEQ ID NO 36
<211> LENGTH: 246
<212> TYPE: PRT
<213> ORGANISM: Artificial Sequence
<220> FEATURE:
<223> OTHER INFORMATION: Synthesized

<400> SEQUENCE: 36

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Ser Gly Gly Gly Gly
        115                 120                 125

Ser Gln Val Gln Leu Arg Gln Ser Gly Pro Glu Leu Val Lys Pro Gly
130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
                245

<210> SEQ ID NO 37
<211> LENGTH: 199
<212> TYPE: PRT

<213> ORGANISM: Artificial Sequence
<220> FEATURE:
<223> OTHER INFORMATION: Synthesized

<400> SEQUENCE: 37

```
Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
                85                  90                  95

His Leu Val Thr Glu Val Arg Gly Met Gln Glu Ala Pro Glu Ala Ile
            100                 105                 110

Leu Ser Lys Ala Val Glu Ile Glu Gln Thr Lys Arg Leu Leu Glu
        115                 120                 125

Gly Met Glu Leu Ile Val Ser Gln Val His Pro Glu Thr Lys Glu Asn
    130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Lys Cys Arg
            180                 185                 190

Ile Ile His Asn Asn Asn Cys
        195
```

<210> SEQ ID NO 38
<211> LENGTH: 240
<212> TYPE: PRT
<213> ORGANISM: Artificial Sequence
<220> FEATURE:
<223> OTHER INFORMATION: Synthesized

<400> SEQUENCE: 38

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Gly Gly Gly Gly Gly Ser Gly Gly Gly Ser Gly Gly Gly Ser
        115                 120                 125
```

```
Asp Ile Val Met Thr Gln Ser Pro Asp Ser Leu Ala Val Ser Leu Gly
        130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
            180                 185                 190

Pro Asp Arg Phe Ser Gly Ser Gly Ser Gly Thr Asp Phe Thr Leu Thr
        195                 200                 205

Ile Ser Ser Leu Gln Ala Glu Asp Val Ala Val Tyr Tyr Cys Thr Gln
210                 215                 220

Ser Phe Ile Leu Arg Thr Phe Gly Gln Gly Thr Lys Val Glu Ile Lys
225                 230                 235                 240

<210> SEQ ID NO 39
<211> LENGTH: 281
<212> TYPE: PRT
<213> ORGANISM: Artificial Sequence
<220> FEATURE:
<223> OTHER INFORMATION: Synthesized

<400> SEQUENCE: 39

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
                20                  25                  30

Ala Ser Leu Glu Glu Ile Val Thr Ile Thr Cys Lys Ala Ser Gln Ala
            35                  40                  45

Ile Asp Ala Tyr Leu Ser Trp Tyr Gln Gln Lys Pro Gly Lys Ser Pro
50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
        115                 120                 125

Gly Gly Gly Gly Ser Gly Gly Gly Ser Gly Gly Gly Gly Ser Met
    130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
    210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255
```

Cys Ala Ser Pro Tyr Tyr Gly Tyr Tyr Phe Pro Phe Asp Tyr Trp Gly
                260                 265                 270

Gln Gly Val Met Val Thr Val Ser Ser
            275                 280

<210> SEQ ID NO 40
<211> LENGTH: 285
<212> TYPE: PRT
<213> ORGANISM: Artificial Sequence
<220> FEATURE:
<223> OTHER INFORMATION: Synthesized

<400> SEQUENCE: 40

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys Gly Gly Gly Gly Ser Gly Gly Gly Ser Gly Gly Gly
    130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
    210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285

<210> SEQ ID NO 41
<211> LENGTH: 242
<212> TYPE: PRT
<213> ORGANISM: Artificial Sequence
<220> FEATURE:
<223> OTHER INFORMATION: Synthesized

<400> SEQUENCE: 41

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65              70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys Gly Gly Gly Gly Ser
            100                 105                 110

Gly Gly Gly Gly Ser Gly Gly Gly Ser Gln Val Thr Leu Lys Glu
        115                 120                 125

Ser Gly Pro Val Leu Val Lys Pro Thr Glu Thr Leu Thr Leu Thr Cys
130             135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Asp Val Tyr Tyr Asn Pro Ser Leu Lys Ser Arg Leu Thr
            180                 185                 190

Ile Thr Lys Asp Ala Ser Lys Asp Gln Val Ser Leu Lys Leu Ser Ser
        195                 200                 205

Val Thr Ala Ala Asp Thr Ala Val Tyr Tyr Cys Val Arg Arg Arg Ala
    210                 215                 220

Thr Gly Thr Gly Phe Asp Tyr Trp Gly Gln Gly Thr Leu Val Thr Val
225                 230                 235                 240

Ser Ser

<210> SEQ ID NO 42
<211> LENGTH: 7902
<212> TYPE: DNA
<213> ORGANISM: Artificial Sequence
<220> FEATURE:
<223> OTHER INFORMATION: Synthesized

<400> SEQUENCE: 42
gtcgacacta gtaatcaacc tctggattac aaaatttgtg aaagattgac tggtattctt      60
aactatgttg ctccttttac gctatgtgga tacgctgctt taatgccttt gtatcatgct     120
attgcttccc gtatggcttt cattttctcc tccttgtata atcctggtt gctgtctctt      180 tatgaggagt tgtggcccgt tgtcaggcaa cgtggcgtgg tgtgcactgt gtttgctgac     240
gcaaccccca ctggttgggg cattgccacc acctgtcagc tcctttccgg gactttcgct     300
ttccccctcc ctattgccac ggcggaactc atcgccgcct gccttgcccg ctgctggaca     360
ggggctcggc tgttgggcac tgacaattcc gtggtgttgt cggggaagct gacgtccttt     420
ccatggctgc tcgcctgtgt tgccacctgg attctgcgcg gacgtccttc tgctacgtc     480 ccttcggccc tcaatccagc ggaccttcct tcccgcggcc tgctgccggc tctgcggcct     540
cttccgcgtc ttcgccttcg ccctcagacg agtcggatct ccctttgggc cgcctccccg     600
cctgccgcgg aattcgagct cggtaccttt aagaccaatg acttacaagg cagctgtaga     660

```
tcttagccac ttttttaaaag aaaaggggggg actggaaggg ctaattcact cccaacgaag    720
acaagatctg cttttttgctt gtactgagtc tctctggtta gaccagatct gagcctggga    780
gctctctggc taactaggga acccactgct taagcctcaa taaagcttgc cttgagtgct    840
tcaagtagtg tgtgcccgtc tgttgtgtga ctctggtaac tagagatccc tcagacccctt   900 ttagtcagtg tggaaaatct ctagcagtag tagttcatgt catcttatta ttcagtattt    960
ataacttgca aagaaatgaa tatcagagag tgagaggaac ttgtttattg cagcttataa   1020
tggttacaaa taaagcaata gcatcacaaa tttcacaaat aaagcatttt tttcactgca   1080
ttctagttgt ggtttgtcca aactcatcaa tgtatcttat catgtctggc tctagctatc   1140
ccgcccctaa ctccgcccat cccgcccta actccgccca gttccgccca ttctccgccc    1200
catggctgac taattttttt tatttatgca gaggccgagg ccgcctcggc ctctgagcta   1260
ttccagaagt agtgaggagg cttttttgga ggcctaggga cgtacccaat tcgccctata   1320
gtgagtcgta ttacgcgcgc tcactggccg tcgttttaca acgtcgtgac tgggaaaacc   1380
ctggcgttac ccaacttaat cgccttgcag cacatccccc tttcgccagc tggcgtaata   1440
gcgaagaggc ccgcaccgat cgcccttccc aacagttgcg cagcctgaat ggcgaatggg   1500
acgcgccctg tagcggcgca ttaagcgcgg cgggtgtggt ggttacgcgc agcgtgaccg   1560
ctacacttgc cagcgcccta gcgcccgctc ctttcgcttt cttcccttcc tttctcgcca   1620
cgttcgccgg ctttccccgt caagctctaa atcgggggct ccctttaggg ttccgattta   1680
gtgctttacg gcacctcgac cccaaaaaac ttgattaggg tgatggttca cgtagtgggc   1740
catcgccctg atagacggtt tttcgccctt tgacgttgga gtccacgttc tttaatagtg   1800
gactcttgtt ccaaactgga acaacactca accctatctc ggtctattct tttgatttat   1860
aagggatttt gccgatttcg gcctattggt taaaaaatga gctgatttaa caaaaattta   1920
acgcgaattt taacaaaata ttaacgctta caatttaggt ggcactttc ggggaaatgt    1980 gcgcggaacc cctatttgtt tatttttcta aatacattca aatatgtatc cgctcatgag   2040
acaataaccc tgataaatgc ttcaataata ttgaaaaagg aagagtatga gtattcaaca   2100
tttccgtgtc gcccttattc ccttttttgc ggcattttgc cttcctgttt ttgctcaccc   2160
agaaacgctg gtgaaagtaa aagatgctga agatcagttg ggtgcacgag tgggttacat   2220
cgaactggat ctcaacagcg gtaagatcct tgagagtttt cgccccgaag aacgttttcc   2280
aatgatgagc acttttaaag ttctgctatg tggcgcggta ttatcccgta ttgacgccgg   2340
gcaagagcaa ctcggtcgcc gcatacacta ttctcagaat gacttggttg agtactcacc   2400
agtcacagaa aagcatctta cggatggcat gacagtaaga gaattatgca gtgctgccat   2460
aaccatgagt gataacactg cggccaactt acttctgaca acgatcggag gaccgaagga   2520
gctaaccgct tttttgcaca acatggggga tcatgtaact cgccttgatc gttgggaacc   2580
ggagctgaat gaagccatac caaacgacga gcgtgacacc acgatgcctg tagcaatggc   2640
aacaacgttg cgcaaactat taactggcga actacttact ctagcttccc ggcaacaatt   2700
aatagactgg atggaggcgg ataaagttgc aggaccactt ctgcgctcgg cccttccggc   2760
tggctggttt attgctgata atctggagc cggtgagcgt ggctctcgcg gtatcattgc    2820
agcactgggg ccagatggta agccctcccg tatcgtagtt atctacacga cggggagtca   2880
ggcaactatg gatgaacgaa atagacagat cgctgagata ggtgcctcac tgattaagca   2940
ttggtaactg tcagaccaag tttactcata tatactttag attgatttaa aacttcattt   3000
```

```
ttaatttaaa aggatctagg tgaagatcct ttttgataat ctcatgacca aaatccctta    3060
acgtgagttt tcgttccact gagcgtcaga ccccgtagaa aagatcaaag gatcttcttg    3120
agatcctttt tttctgcgcg taatctgctg cttgcaaaca aaaaaaccac cgctaccagc    3180
ggtggtttgt ttgccggatc aagagctacc aactcttttt ccgaaggtaa ctggcttcag    3240
cagagcgcag ataccaaata ctgttcttct agtgtagccg tagttaggcc accacttcaa    3300
gaactctgta gcaccgccta catacctcgc tctgctaatc ctgttaccag tggctgctgc    3360
cagtggcgat aagtcgtgtc ttaccgggtt ggactcaaga cgatagttac cggataaggc    3420
gcagcggtcg ggctgaacgg ggggttcgtg cacacagccc agcttggagc gaacgaccta    3480
caccgaactg agatacctac agcgtgagct atgagaaagc gccacgcttc ccgaagggag    3540
aaaggcggac aggtatccgg taagcggcag ggtcggaaca ggagagcgca cgagggagct    3600
tccaggggga aacgcctggt atctttatag tcctgtcggg tttcgccacc tctgacttga    3660
gcgtcgattt ttgtgatgct cgtcaggggg cggagcctat ggaaaaacg ccagcaacgc    3720 ggccttttta cggttcctgg ccttttgctg gccttttgct cacatgttct ttcctgcgtt    3780
atcccctgat tctgtggata accgtattac cgcctttgag tgagctgata ccgctcgccg    3840
cagccgaacg accgagcgca gcgagtcagt gagcgaggaa gcggaagagc gcccaatacg    3900
caaaccgcct ctccccgcgc gttggccgat tcattaatgc agctggcacg acaggtttcc    3960
cgactggaaa gcgggcagtg agcgcaacgc aattaatgtg agttagctca ctcattaggc    4020
accccaggct ttacacttta tgcttccggc tcgtatgttg tgtggaattg tgagcggata    4080
acaatttcac acaggaaaca gctatgacca tgattacgcc aagcgcgcaa ttaaccctca    4140
ctaaagggaa caaaagctgg agctgcaagc ttaatgtagt cttatgcaat actcttgtag    4200
tcttgcaaca tggtaacgat gagttagcaa catgccttac aaggagagaa aaagcaccgt    4260
gcatgccgat tggtggaagt aaggtggtac gatcgtgcct tattaggaag gcaacagacg    4320
ggtctgacat ggattggacg aaccactgaa ttgccgcatt gcagagatat tgtatttaag    4380
tgcctagctc gatacataaa cggctctctc tggttagacc agatctgagc ctgggagctc    4440
tctggctaac tagggaaccc actgcttaag cctcaataaa gcttgccttg agtgcttcaa    4500
gtagtgtgtg cccgtctgtt gtgtgactct ggtaactaga gatccctcag accctttag    4560 tcagtgtgga aaatctctag cagtggcgcc cgaacaggga cttgaaagcg aaagggaaac    4620
cagaggagct ctctcgacgc aggactcggc ttgctgaagc gcgcacggca agaggcgagg    4680
ggcggcgact ggtgagtacg ccaaaaattt tgactagcgg aggctagaag gagagagatg    4740
ggtgcgagag cgtcagtatt aagcggggga gaattagatc gcgatgggaa aaaattcggt    4800
taaggccagg gggaaagaaa aaatataaat taaaacatat agtatgggca agcagggagc    4860
tagaacgatt cgcagttaat cctggcctgt tagaaacatc agaaggctgt agacaaatac    4920
tgggacagct acaaccatcc cttcagacag gatcagaaga acttagatca ttatataata    4980
cagtagcaac cctctattgt gtgcatcaaa ggatagagat aaaagacacc aaggaagctt    5040
tagacaagat agaggaagag caaaacaaaa gtaagaccac cgcacagcaa gcggccgctg    5100
atcttcagac ctggaggagg agatatgagg gacaattgga gaagtgaatt atataaatat    5160
aaagtagtaa aaattgaacc attaggagta gcacccacca aggcaaagag aagagtggtg    5220
cagagagaaa aaagagcagt gggaatagga gctttgttcc ttgggttctt gggagcagca    5280
ggaagcacta tgggcgcagc gtcaatgacg ctgacggtac aggccagaca attattgtct    5340
ggtatagtgc agcagcagaa caatttgctg agggctattg aggcgcaaca gcatctgttg    5400
```

```
caactcacag tctggggcat caagcagctc caggcaagaa tcctggctgt ggaaagatac    5460
ctaaaggatc aacagctcct ggggatttgg ggttgctctg gaaaactcat ttgcaccact    5520
gctgtgcctt ggaatgctag ttggagtaat aaatctctgg aacagatttg aatcacacg     5580 acctggatgg agtgggacag agaaattaac aattacacaa gcttaataca ctccttaatt    5640
gaagaatcgc aaaccagca agaaaagaat gaacaagaat tattggaatt agataaatgg    5700
gcaagtttgt ggaattggtt taacataaca aattggctgt ggtatataaa attattcata    5760
atgatagtag gaggcttggt aggtttaaga atagttttg ctgtactttc tatagtgaat     5820
agagttaggc agggatattc accattatcg tttcagaccc acctcccaac cccgagggga    5880
cccgacaggc ccgaaggaat agaagaagaa ggtggagaga gagacagaga cagatccatt    5940
cgattagtga acggatctcg acggtatcga tcacgagact agcctcgaca caaatggcag    6000
tattcatcca caattttaaa agaaagggg ggattggggg gtacagtgca ggggaaagaa     6060
tagtagacat aatagcaaca gacatacaaa ctaaagaatt acaaaaacaa attacaaaaa    6120
ttcaaaattt tcgggtttat tacagggaca gcagaaatcc actttggctc gagaagcttg    6180
atatcggctc cggtgcccgt cagtgggcag agcgcacatc gcccacagtc cccgagaagt    6240 tgggggagg ggtcggcaat tgaaccggtg cctagagaag gtggcgcggg gtaaactggg     6300
aaagtgatgt cgtgtactgg ctccgccttt tcccgaggg tggggagaa ccgtatataa      6360 gtgcagtagt cgccgtgaac gttctttttc gcaacgggtt tgccgccaga acacaggatc    6420
cgccaccatg gccttaccag tgaccgcctt gctcctgccg ctggccttgc tgctccacgc    6480
cgccaggccg gatatccaga tgacccagag cccgagcagc ctgagcgcga gcgtgggtga    6540
tcgcgtgacc attacctgca gggcaagtca ggacattagt aaatatttaa attggtatca    6600
gcagaaaccg ggtaaagcgc cgaaactgtt aatttatcat acatcaagat tacactcagg    6660
cgtgccgtcg cgttttagcg gctcgggttc gggcaccgat tttaccctga ccatctcgag    6720
cttgcagccg gaggacttcg ccacctacta ttgccaacag ggtaatacgc ttccgtacac    6780
gttcggtcag ggcaccaaag tggagatcaa aggtggcgt ggctcgggcg gtggtgggtc      6840
gggtggcggc ggatctgagg tgcagctggt ggagtctggg ggaggcttgg tacagcctgg    6900
ggggtccctg agactctcct gtgcagcctc tggagtgtcc ctgcctgatt atggcgtgtc    6960
ctgggtccgc caggctccag ggaaggggct ggagtgggtt tcagtgatct ggggcagcga    7020
gacaacctac tacaacagcg ccctgaagtc ccgattcacc atctccagag acaatgccaa    7080
gaactcactg tatctgcaaa tgaacagcct gagagccgag acacggctg tgtattactg     7140 tgcgaagcac tactactacg gcggcagcta cgctatggac tactggggcc aaggaaccct    7200
ggtcaccgtg tcctcaacca cgacgccagc gccgcgacca ccaacaccgg cgcccaccat    7260
cgcgtcgcag cccctgtccc tgcgcccaga ggcgtgccgg ccagcggcgg ggggcgcagt    7320
gcacacgagg gggctggact tcgcctgtga tatctcacatc tgggcgccct tggccgggac   7380
ttgtggggtc cttctcctgt cactggttat cacccttttac tgcaaacggg cagaaagaa    7440 actcctgtat atattcaaac aaccatttat gagaccagta caaactactc aagaggaaga    7500
tggctgtagc tgccgatttc cagaagaaga agaaggagga tgtgaactga gagtgaagtt    7560
cagcaggagc gcagacgccc ccgcgtacaa gcagggccag aaccagctct ataacgagct    7620
caatctagga cgaagagagg agtacgatgt tttggacaag aggcgtggcc gggaccctga    7680
gatgggggga aagccgagaa ggaagaaccc tcaggaaggc ctgtacaatg aactgcagaa    7740
```

-continued

```
agataagatg gcggaggcct acagtgagat tgggatgaaa ggcgagcgcc ggaggggcaa    7800
ggggcacgat ggcctttacc agggtctcag tacagccacc aaggacacct acgacgccct    7860
tcacatgcag gccctgcccc ctcgctaatc tagaggcgcg cc                       7902
```

<210> SEQ ID NO 43

<400> SEQUENCE: 43

000

<210> SEQ ID NO 44
<211> LENGTH: 15
<212> TYPE: PRT
<213> ORGANISM: Artificial Sequence
<220> FEATURE:
<223> OTHER INFORMATION: Synthesized

<400> SEQUENCE: 44

```
Gly Gly Gly Gly Ser Gly Gly Gly Gly Ser Gly Gly Gly Gly Ser
1               5                  10                  15
```

<210> SEQ ID NO 45
<211> LENGTH: 30
<212> TYPE: PRT
<213> ORGANISM: Artificial Sequence
<220> FEATURE:
<223> OTHER INFORMATION: Synthesized

<400> SEQUENCE: 45

```
Ser Met Asp Phe Lys Ser Asn Ser Ala Val Ala Trp Ser Asn Lys Ser
1               5                  10                  15

Asp Phe Ala Cys Ala Asn Ala Phe Asn Asn Ser Ile Ile Pro
            20                  25                  30
```

<210> SEQ ID NO 46
<211> LENGTH: 89
<212> TYPE: DNA
<213> ORGANISM: Artificial Sequence
<220> FEATURE:
<223> OTHER INFORMATION: Synthesized

<400> SEQUENCE: 46

```
tctatggact tcaagagcaa cagtgctgtg gcctggagca acaaatctga ctttgcatgt    60
gcaaacgcct tcaacaacag cattattcc                                      89
```